US012779161B2

(12) United States Patent
Xu et al.

(10) Patent No.: US 12,779,161 B2
(45) Date of Patent: Nov. 3, 2026

(54) FACIAL SIZE DETERMINATION METHOD AND APPARATUS

(71) Applicant: BMC (TIANJIN) MEDICAL CO., LTD., Tianjin (CN)

(72) Inventors: Jian Xu, Tianjin (CN); Huiquan Wang, Tianjin (CN); Mingzhao Zhou, Tianjin (CN); Long He, Tianjin (CN); Zhi Zhuang, Tianjin (CN)

(73) Assignee: BMC (TIANJIN) MEDICAL CO., LTD., Tianjin (CN)

( * ) Notice: Subject to any disclaimer, the term of this patent is extended or adjusted under 35 U.S.C. 154(b) by 720 days.

(21) Appl. No.: 18/266,302

(22) PCT Filed: Jan. 25, 2022

(86) PCT No.: PCT/CN2022/073708

§ 371 (c)(1),
(2) Date: Jun. 9, 2023

(87) PCT Pub. No.: WO2022/156810

PCT Pub. Date: Jul. 28, 2022

(65) Prior Publication Data

US 2024/0024604 A1 Jan. 25, 2024

(30) Foreign Application Priority Data

Jan. 25, 2021 (CN) ......................... 202110100112.4

(51) Int. Cl.
*A61M 16/06* (2006.01)

(52) U.S. Cl.
CPC ..... *A61M 16/0605* (2014.02); *A61M 2230/00* (2013.01)

(58) Field of Classification Search
CPC .......... A61M 16/0605; A61M 2230/00; G06V 10/243; G06V 10/255; G06V 40/171; G06V 40/166; G06V 40/161
See application file for complete search history.

(56) References Cited

U.S. PATENT DOCUMENTS 9,536,301 B1 1/2017 Maurer et al.
2009/0060394 A1* 3/2009 Yamazaki ............ G06V 10/242
382/311

(Continued)

FOREIGN PATENT DOCUMENTS

CN 106482641 A 3/2017
CN 106666903 A 5/2017

(Continued)

*Primary Examiner* — Vu Le
*Assistant Examiner* — Rachel Anne Ometz
(74) *Attorney, Agent, or Firm* — Bayramoglu Law Offices LLC

(57) ABSTRACT

A method and apparatus for determining a human-face size are provided. The method includes: collecting a first to-be-measured human-face image of a to-be-measured target, wherein the first to-be-measured human-face image includes a first to-be-measured human face of the to-be-measured target and a circular reference object; acquiring a first pixel value of the first to-be-measured human face, and a second pixel value of the circular reference object; in response to a circularity of the circular reference object being greater than a preset circularity threshold, acquiring an angle of inclination of the circular reference object; and according to the first pixel value, the second pixel value, the angle of inclination and an actual size of the circular reference object, determining a first size of the first to-be-measured human face.

15 Claims, 10 Drawing Sheets

(56) References Cited

U.S. PATENT DOCUMENTS

| | | | | |
|---|---|---|---|---|
| 2012/0169868 | A1 | 7/2012 | Bae et al. | |
| 2017/0124383 | A1* | 5/2017 | Ohbitsu | G06T 7/74 |
| 2017/0278272 | A1* | 9/2017 | Ravindra | G06T 11/00 |
| 2018/0117272 | A1* | 5/2018 | Fu | A61M 16/06 |
| 2018/0299704 | A1* | 10/2018 | Fonte | G02C 13/005 |
| 2021/0361897 | A1* | 11/2021 | Neal | A61B 5/1071 |

FOREIGN PATENT DOCUMENTS

| | | | |
|---|---|---|---|
| CN | 108240793 | A | 7/2018 |
| CN | 109118426 | A | 1/2019 |
| CN | 109148433 | A | 1/2019 |
| CN | 109840453 | A | 6/2019 |
| CN | 110348936 | A | 10/2019 |
| CN | 111259703 | A | 6/2020 |
| CN | 111486798 | A | 8/2020 |
| CN | 111932604 | A | 11/2020 |
| CN | 112070021 | A | 12/2020 |
| CN | 112254633 | A | 1/2021 |
| CN | 112883811 | A | 6/2021 |

* cited by examiner

FACIAL SIZE DETERMINATION METHOD AND APPARATUS

CROSS REFERENCE TO THE RELATED APPLICATIONS

This application is the national phase entry of International Application No. PCT/CN2022/073708, filed on Jan. 25, 2022, which is based upon and claims priority to Chinese Patent Application No. 202110100112.4, filed on Jan. 25, 2021, the entire contents of which are incorporated herein by reference.

TECHNICAL FIELD

The present disclosure relates to the technical field of image processing, and particularly relates to a method and apparatus for determining a human-face size.

BACKGROUND

A method of non-invasive positive-pressure ventilation has been extensively used in Obstructive Sleep Apnea Syndrome (referred to for short as OSA), Chronic Obstructive Pulmonary Disease (referred to for short as COPD) and so on. No pipe is required to be inserted into the airway of the patient by surgery, but by using a blower, a pipeline and a patient interface device, a continuous pressure ventilation (CPAP) or varying pressure ventilation is delivered to the airway of the patient, for example, a double-level pressure varying with the respiratory cycle of the patient or an automatically regulated pressure ventilation varying with the monitored situation of the patient. Such a pressure-supporting therapy is usually also used in obstructive hypopnea, Upper Airway Resistance Syndrome (referred to for short as UARS), congestive heart failure and so on.

Non-invasive ventilation treatment device includes the interface device on the face of the patient. Such an interface device generally refers to a face mask that surrounds the nose and the mouth of the face of the patient and seals them. In the treatment, an external blower is the pressure supporting device, for example, a breathing machine, and the patient interface device connects the gas pressure supplied by the breathing machine and the airway of the patient, to send the respiratory air flow to the airway of the patient.

In order to adapt for different face sizes, in many cases the face masks are set to be different models, such as a large size, a middle size and a small size. In order to provide a more effective treatment, it is required to select the face mask that is suitable for the size of the face of the patient. When a face mask that does not match with the face size is selected, air leakage or other problem might happen, which affects the wearing comfortableness, and deteriorates the effect of the treatment. Therefore, it is very important to conveniently and quickly measure the face size of the patient, thereby selecting the face mask that is suitable for the face size of the patient. Regarding a patient having a malformed face, the face masks of the standard models cannot be used, and it is required to customize a dedicated face mask according to the contour of the face of the patient. In this case, it is required to conveniently and quickly acquire the 3D contour information of the face of the patient.

In the selection or personalized designing of medical face masks, a nose measuring card shown in FIG. 1 is usually used to measure the nose width. Most of the nose measuring cards for measuring the nose width in the related art are a card that can accommodate the nose of the patient. Regarding the nose measuring card shown in FIG. 1, the nose measuring card, according to the applicable models of face masks, is provided with three slots (10-12) of a small size (S), a middle size (M) and a large size (L), and corresponding model identifiers 2 are under the slots. In usage, the patient clips the slots of the nose measuring card on the nose, and, by using the model identifiers 2 on the nose measuring card, selects the suitable face-mask model.

In the related art, in the selection or personalized designing of the medical face masks, a measuring tool such as a scale ruler as shown in FIG. 2 may also be used to directly measure specific sizes of the face of the patient (for example, the 5 sizes in FIG. 2). According to those sizes in the human face, model selection or personalized designing of the face mask is performed.

The method of measuring the nose width by using the nose measuring card in the related art, in an aspect, can merely obtain an approximate range of the nose width of the patient, and cannot be used for the personalized customization of the face mask. In another aspect, when the model selection of the face mask is performed merely by using the nose width, the single factor is taken into consideration, and unsuitableness at the other positions such as the bridge of the nose and the chin might happen.

The method of directly measuring the face size of the patient by using a scale ruler in the related art has tedious data recording and troublesome operation, and the manual measurement easily has a high error.

In view of the above problems, no effective solutions have been proposed at present.

SUMMARY

The embodiments of the present disclosure provide a method and apparatus for determining a human-face size, which may accurately measure the human-face size of the to-be-measured target, to solve the technical problem in the related art of a low precision of measurement on human-face sizes.

In the first aspect, an embodiment of the present disclosure provides a method for determining a human-face size, where the method includes:

collecting a first to-be-measured human-face image of a to-be-measured target, where the first to-be-measured human-face image includes a first to-be-measured human face of the to-be-measured target and a circular reference object;

acquiring a first pixel value of the first to-be-measured human face, and a second pixel value of the circular reference object;

in response to a circularity of the circular reference object being greater than a preset circularity threshold, acquiring an angle of inclination of the circular reference object; and according to the first pixel value, the second pixel value, the angle of inclination and an actual size of the circular reference object, determining a first size of the first to-be-measured human face.

In the second aspect, an embodiment of the present disclosure further provides a method for determining a human-face size, where the method includes:

by using a second image collecting device, collecting a second to-be-measured human-face image and a third to-be-measured human-face image of a to-be-measured target, where an image-collection distance of the second to-be-measured human-face image and an image-collection distance of the third to-be-measured human-face image are unequal;

acquiring a second pixel value of the second to-be-measured human-face image, and a third pixel value of the third to-be-measured human-face image; and according to an image-collection-distance difference between the second to-be-measured human-face image and the third to-be-measured human-face image, a focal length of the second image collecting device, the second pixel value and the third pixel value, determining a second size of a second to-be-measured human face of the to-be-measured target.

In the third aspect, an embodiment of the present disclosure further provides a method for determining a human-face size, where the method includes:

by using a third image collecting device, collecting a fourth to-be-measured human-face image of a to-be-measured target, where the third image collecting device includes at least two cameras;

acquiring at least two incident angles of inclination corresponding to information collecting points in the fourth to-be-measured human-face image, where the incident angles of inclination are obtained based on the third image collecting device when diffuse reflection from the information collecting points irradiates into the at least two cameras;

according to the at least two incident angles of inclination and a camera distance between the at least two cameras, determining positions of the information collecting points; and according to the positions of the information collecting points, determining a third size of a third to-be-measured human face in the fourth to-be-measured human-face image.

In the fourth aspect, an embodiment of the present disclosure further provides a method for determining a face-mask model, where the method includes:

by using the method for determining a human-face size according to any one of the first aspect, the second aspect and the third aspect, obtaining a target human-face size; and according to a plurality of groups of preset face-mask reference values and the target human-face size, determining a face-mask model of the to-be-measured target, where the plurality of groups of preset face-mask reference values correspond to a plurality of face-mask models.

In the fifth aspect, an embodiment of the present disclosure further provides an apparatus for determining a human-face size, where the apparatus includes:

a first collecting unit configured for collecting a first to-be-measured human-face image of a to-be-measured target, where the first to-be-measured human-face image includes a first to-be-measured human face of the to-be-measured target and a circular reference object;

a first acquiring unit configured for acquiring a first pixel value of the first to-be-measured human face, and a second pixel value of the circular reference object;

a second acquiring unit configured for, in response to a circularity of the circular reference object being greater than a preset circularity threshold, acquiring an angle of inclination of the circular reference object; and a first determining unit configured for, according to the first pixel value, the second pixel value, the angle of inclination and an actual size of the circular reference object, determining a first size of the first to-be-measured human face.

In the sixth aspect, an embodiment of the present disclosure further provides an apparatus for determining a human-face size, where the apparatus includes:

a second collecting unit configured for, by using a second image collecting device, collecting a second to-be-measured human-face image and a third to-be-measured human-face image of a to-be-measured target, where an image-collection distance of the second to-be-measured human-face image and an image-collection distance of the third to-be-measured human-face image are unequal;

a third acquiring unit configured for acquiring a second pixel value of the second to-be-measured human-face image, and a third pixel value of the third to-be-measured human-face image; and a second determining unit configured for, according to an image-collection-distance difference between the second to-be-measured human-face image and the third to-be-measured human-face image, a focal length of the second image collecting device, the second pixel value and the third pixel value, determining a second size of a second to-be-measured human face of the to-be-measured target.

In the seventh aspect, an embodiment of the present disclosure further provides an apparatus for determining a human-face size, where the apparatus includes:

a third collecting unit configured for, by using a third image collecting device, collecting a fourth to-be-measured human-face image of a to-be-measured target, where the third image collecting device includes at least two cameras;

a fourth acquiring unit configured for acquiring at least two incident angles of inclination corresponding to information collecting points in the fourth to-be-measured human-face image, where the incident angles of inclination are obtained based on the third image collecting device when diffuse reflection from the information collecting points irradiates into the at least two cameras;

a third determining unit configured for, according to the at least two incident angles of inclination and a camera distance between the at least two cameras, determining positions of the information collecting points; and a fourth determining unit configured for, according to the positions of the information collecting points, determining a third size of a third to-be-measured human face in the fourth to-be-measured human-face image.

The embodiments of the present disclosure have the following advantages:

An embodiment of the present disclosure includes collecting a first to-be-measured human-face image of a to-be-measured target, where the first to-be-measured human-face image includes a first to-be-measured human face of the to-be-measured target and a circular reference object; acquiring a first pixel value of the first to-be-measured human face, and a second pixel value of the circular reference object; in response to a circularity of the circular reference object being greater than a preset circularity threshold, acquiring an angle of inclination of the circular reference object; and according to the first pixel value, the second pixel value, the angle of inclination and an actual size of the circular reference object, determining a first size of the first to-be-measured human face. By using the proportion relation between the actual size and the pixel value in the first to-be-measured human-face image of the circular reference object, and according to the angle of inclination of the circular reference object, the first size of the first to-be-measured human face is determined, which simplifies the steps of the measuring operation in the related art, and increases the accuracy of the measurement on the human-face size.

Furthermore, another embodiment of the present disclosure includes by using a second image collecting device, collecting a second to-be-measured human-face image and a third to-be-measured human-face image of a to-be-measured target, where an image-collection distance of the second to-be-measured human-face image and an image-collection distance of the third to-be-measured human-face image are unequal; acquiring a second pixel value of the second to-be-measured human-face image, and a third pixel value of the third to-be-measured human-face image; and according to an image-collection-distance difference between the second to-be-measured human-face image and the third to-be-measured human-face image, a focal length of the second image collecting device, the second pixel value and the third pixel value, determining a second size of a second to-be-measured human face of the to-be-measured target. By photographing the plurality of human-face images of the to-be-measured target at unequal image-collection distances, and subsequently using the image-collection-distance difference and the pixel values of the different human-face images, the second size of the second to-be-measured human face is determined, which further increases the accuracy of the measurement on the human-face size.

Furthermore, another embodiment of the present disclosure includes by using a third image collecting device, collecting a fourth to-be-measured human-face image of a to-be-measured target, where the third image collecting device includes at least two cameras; acquiring at least two incident angles of inclination corresponding to information collecting points in the fourth to-be-measured human-face image, where the incident angles of inclination are obtained based on the third image collecting device when diffuse reflection from the information collecting points irradiates into the at least two cameras; according to the at least two incident angles of inclination and a camera distance between the at least two cameras, determining positions of the information collecting points; and according to the positions of the information collecting points, determining a third size of a third to-be-measured human face in the fourth to-be-measured human-face image. That avoids manually measuring the human face by using a scale ruler, which simplifies the measuring operation. Moreover, by photographing the fourth to-be-measured human-face image by using a plurality of lenses, the third size of the third to-be-measured human face may be determined based on the camera distance between the cameras, which ensures the accuracy of the measurement on the human-face size.

The above description is merely a summary of the technical solutions of the present disclosure. In order to more clearly know the elements of the present disclosure to enable the implementation according to the contents of the description, and in order to make the above and other purposes, features and advantages of the present disclosure more apparent and understandable, the particular embodiments of the present disclosure are provided below.

BRIEF DESCRIPTION OF THE DRAWINGS

In order to more clearly illustrate the technical solutions of the embodiments of the present disclosure, the figures that are required to describe the embodiments of the present disclosure will be briefly described below. Apparently, the figures that are described below are embodiments of the present disclosure, and a person skilled in the art can obtain other figures according to these figures without paying creative work.

DETAILED DESCRIPTION OF THE EMBODIMENTS

The technical solutions of the embodiments of the present disclosure will be clearly and completely described below with reference to the drawings of the embodiments of the present disclosure. Apparently, the described embodiments are merely certain embodiments of the present disclosure, rather than all of the embodiments. All of the other embodiments that a person skilled in the art obtains on the basis of the embodiments of the present disclosure without paying creative work fall within the protection scope of the present disclosure.

The First Method Embodiment

Figure 1:
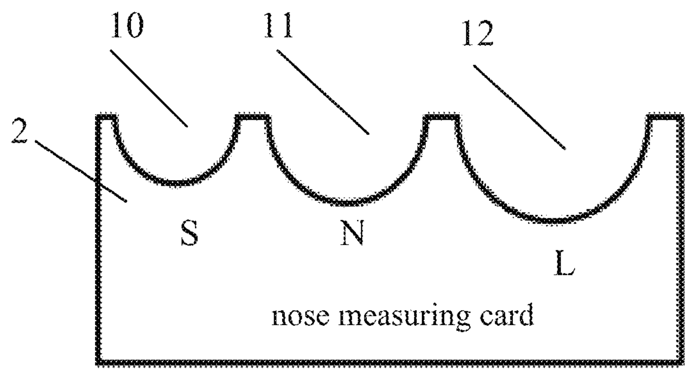
FIG. 1 (Prior Art)
FIG. 1 shows a schematic diagram of a nose measuring card in the related art.
Figure 2:
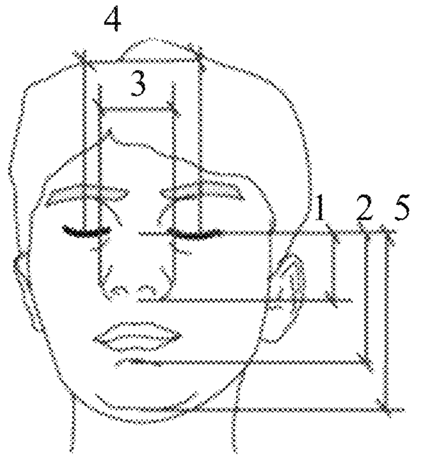
FIG. 2 (Prior Art)
FIG. 2 shows a schematic diagram of the direct measurement on a particular size of the face of a patient by using a measuring tool such as a scale ruler in the related art.
Figure 3:
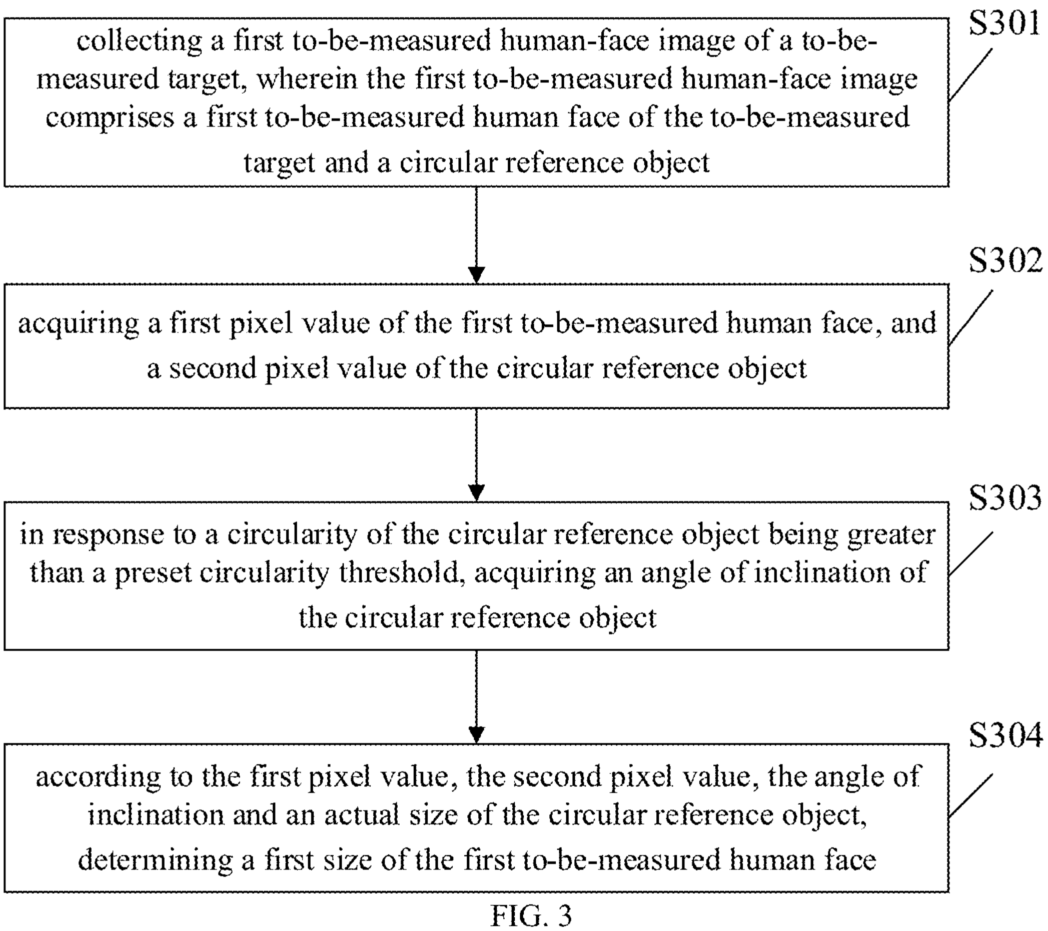
FIG. 3 shows a flow chart of the first embodiment of the method for determining a human-face size according to the present disclosure.

Referring to FIG. 3, FIG. 3 shows a flow chart of the first embodiment of the method for determining a human-face size according to the present disclosure. The method may particularly include:

- S301: collecting a first to-be-measured human-face image of a to-be-measured target, where the first to-be-measured human-face image includes a first to-be-measured human face of the to-be-measured target and a circular reference object;
- S302: acquiring a first pixel value of the first to-be-measured human face, and a second pixel value of the circular reference object;
- S303: in response to a circularity of the circular reference object being greater than a preset circularity threshold, acquiring an angle of inclination of the circular reference object; and
- S304: according to the first pixel value, the second pixel value, the angle of inclination and an actual size of the circular reference object, determining a first size of the first to-be-measured human face.

In the present embodiment, a first to-be-measured human-face image of a to-be-measured target is collected, where the first to-be-measured human-face image may be a photograph of the whole or a local part of a human body. The first to-be-measured human-face image includes the first to-be-measured human face that is required to be measured and a preset reference object, for example, a photograph of the full body, a photograph of the upper half body, a photograph of the head or the face, and so on, of a human body, which is not limited in any form in the present embodiment. The first image collecting device according to the present embodiment generally collects a planar image of the to-be-measured target, and the first image collecting device includes but is not limited to a photo camera, a video camera and other devices that have the function of image collection.

In the present embodiment, the circular reference object includes but is not limited to a coin, a circular cup cover, a circular disk and so on. Furthermore, the preset reference object further includes but is not limited to a circular scrip of a known size. In the present embodiment, the particular type and shape of the circular reference object are not limited in any form. The circularity according to the present embodiment refers to the difference between the radii of two concentric circles that include the same actual cross-sectional contour and have the lowest radius difference. The lower the value of the difference is, which indicates that the circle more tends to be a standard circle, and the higher the value of the difference is, which indicates that the circle deviates from a standard circle.

Figure 4:
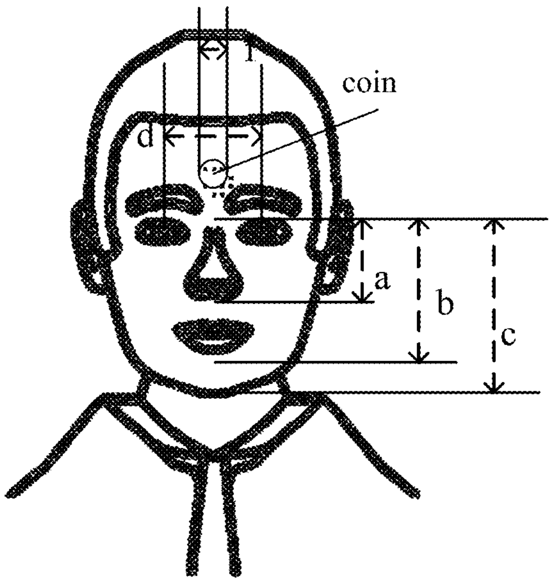
FIG. 4 shows a schematic diagram of a first to-be-measured human-face image at a standard angle according to the present disclosure.

Furthermore, when the circularity of the circular reference object is less than or equal to the preset circularity threshold, it is deemed that, currently, the plane of the circular reference object and the plane where the image collecting device is located are parallel. Referring to FIG. 4, FIG. 4 shows the circular reference object that is placed on a forehead. In particular application scenes, the circular reference object includes but is not limited to a coin, a circular scrip and so on. In the case that the image-collection angle when the collecting device is collecting the first to-be-measured human-face image of the to-be-measured target is a standard angle, for example, the central axis of the lens of the camera is perpendicular to the plane of the circular reference object, or the camera is parallel to the plane of the circular reference object of the human face, then the circular reference object is presented as a standard circle in the first to-be-measured human-face image.

Figure 5:
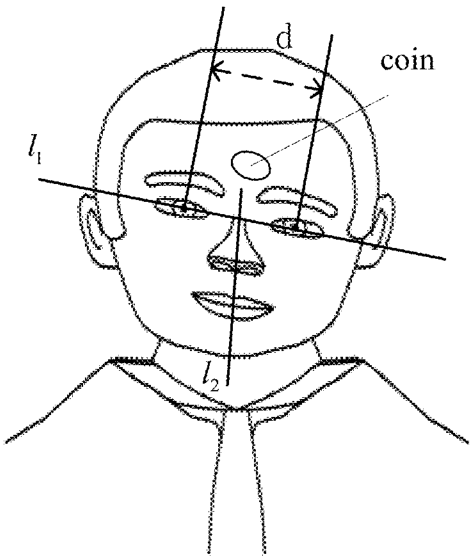
FIG. 5 shows a schematic diagram of a first to-be-measured human-face image at a non-standard angle according to the present disclosure.

However, in the case that the image-collection angle when the collecting device is collecting the first to-be-measured human-face image of the to-be-measured target is a non-standard angle, the circularity of the circular reference object is greater than the preset circularity threshold, and therefore it is required to acquire the angle of inclination of the circular reference object. Referring to FIG. 5, FIG. 5 shows a schematic diagram of a first to-be-measured human-face image at a non-standard angle according to the present disclosure. When the image-collection angle is a non-standard angle, the circularity of the circular reference object increases, and the circular reference object is presented as an ellipse. In this case, when the first size of the first human face is determined according to the pixel value and the actual size of the circular reference object, a measurement deviation emerges.

When the circularity of the circular reference object is greater than a preset circularity threshold, it is determined that the first to-be-measured human face including the circular reference object is photographed at a non-standard angle, and accordingly it is deemed that the first to-be-measured human-face image is a projection on the photograph/negative film. Therefore, it is required to determine the angle of inclination of the circular reference object, to rectify the deviation of the angle of inclination. Therefore, when the circularity of the circular reference object in the first to-be-measured human-face image is greater than the preset circularity threshold, it is required to determine the angle of inclination of the circular reference object, and, after the angle of inclination of the circular reference object is determined, the first size of the first to-be-measured human face according to the angle of inclination is subsequently determined.

In other examples of the present embodiment, on the above basis, the coin adhered to the forehead of the to-be-measured target is replaced by a credit card, which, certainly, may also be a circular non-standard item whose size may be easily measured (including but not limited to a circular scrip). The implementations and the calculation processes of the other examples of the present embodiment are the same as the principle when a coin is used as the preset reference object, and are not discussed further herein.

It should be noted that the present embodiment includes collecting a first to-be-measured human-face image of a to-be-measured target, where the first to-be-measured human-face image includes a first to-be-measured human face of the to-be-measured target and a circular reference object; acquiring a first pixel value of the first to-be-measured human face, and a second pixel value of the circular reference object; if a circularity of the circular reference object is greater than a preset circularity threshold, acquiring an angle of inclination of the circular reference object; and according to the first pixel value, the second pixel value, the angle of inclination and an actual size of the circular reference object, determining a first size of the first to-be-measured human face. By using the proportion relation between the actual size and the pixel value in the first to-be-measured human-face image of the circular reference object, and according to the angle of inclination of the circular reference object, the first size of the first to-be-measured human face is determined, which simplifies the steps of the measuring operation in the related art, and increases the accuracy of the measurement on the human-face size.

Optionally, the present embodiment further includes but is not limited to: if the circularity is less than or equal to the preset circularity threshold, according to the first pixel value, the second pixel value and the actual size, determining the first size.

Particularly, in an example, referring to FIG. 4, FIG. 4 shows a schematic diagram of the first to-be-measured human-face image at a standard angle according to the present disclosure, in which a standardized coin is used as the preset reference object. When the first to-be-measured human-face image of the to-be-measured target is being collected at the standard angle, the coin is pressed at the center of the forehead of the human face of the to-be-measured target. Because the coin is closely adhered to the center of the forehead, it can be understood that the coin and the human face are in the same plane. As a known condition, the diameter of a 1 yuan coin is 22.25 mm. When the image collection is performed at a standard angle, it may be deemed that the camera is parallel to the plane where the human face of the to-be-measured target is located. In this case, the pixel value f of the diameter of the coin in the first to-be-measured human-face image is measured. Accordingly, according to the proportion relation between the actual size and the pixel value in the first to-be-measured human-face image, it may be obtained that:

$$\frac{22.25}{f} = \frac{A}{a} = \frac{B}{b} = \frac{C}{c} = \frac{D}{d} \tag{3}$$

By using the above formula, the actual sizes of the particular positions in the first to-be-measured human face may be obtained as follows:

$$A = \frac{22.25a}{f},\ B = \frac{22.25b}{f},\ C = \frac{22.25c}{f},\ D = \frac{22.25d}{f} \tag{4}$$

By using the above example, in response to the circularity of the circular reference object being less than the preset circularity threshold, the first size of the first to-be-measured human face may be determined according to the first pixel value, the second pixel value and the actual size of the circular reference object, which increases the precision of the acquired human-face size.

Optionally, in the present embodiment, in response to the circularity being greater than the preset circularity threshold, the step of determining the angle of inclination of the circular reference object includes but is not limited to: acquiring a standard major axis of the circular reference object, where the standard major axis refers to, in response to the circularity being greater than the preset circularity threshold, a longest diameter in the circular reference object; acquiring a first major axis in a first direction and a second major axis in a second direction in the circular reference object, where the first direction refers to a straight line where a connecting line between centers of two eyes in the first to-be-measured human-face image is located, and the second direction refers to a straight line where a connecting line between an eyebrow center and a nasal tip in the first to-be-measured human-face image is located; according to the standard major axis and the first major axis, determining a horizontal angle of inclination of the circular reference object; and according to the standard major axis and the second major axis, determining a vertical angle of inclination of the circular reference object.

Particularly, referring to FIG. 5, FIG. 5 shows a schematic diagram of the first to-be-measured human-face image when the preset reference object is a coin. That is because, when the first to-be-measured human-face image of the to-be-measured target is being collected, the orientation of the first image collecting device and the human face of the to-be-measured target have a certain angle of inclination therebetween. In this case, the photograph may be considered as a projection of the contour of the first to-be-measured human face on the paper plane (the plane where the negative film or the roll film is located). In the projection direction, it may be deemed that the above angle of inclination is formed by a horizontal angle of inclination $\alpha$ and a vertical angle of inclination $\beta$. As shown in FIG. 5, the connecting line between the centers of the two eyes in the face plane of the to-be-measured target is defined as $I_1$, and the connecting line of the eyebrow center, the nasal tip and the philtrum (the depression in the middle over the upper lip) is defined as $I_2$. In the space coordinate system, the horizontal angle of inclination $\alpha$ refers to the included angle between the $I_1$ in the face plane and its projection in the paper plane, and the vertical angle of inclination $\beta$ refers to the included angle between the $I_2$ in the face plane and its projection in the paper plane.

Figure 6:
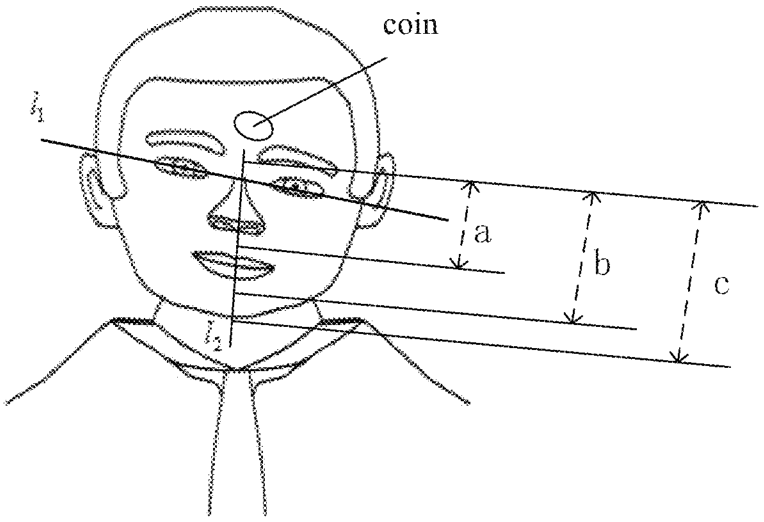
FIG. 6 shows a schematic diagram of a first to-be-measured human-face image including a circular reference object with a circularity greater than a preset threshold according to the present disclosure.
Figure 7:
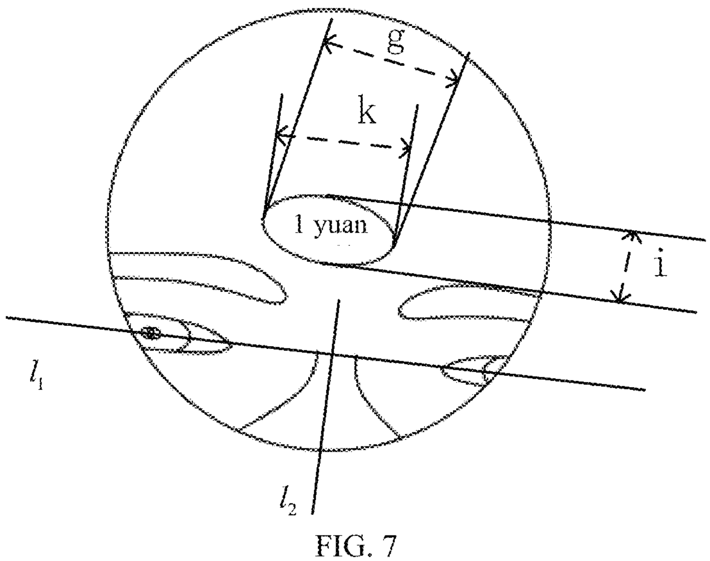
FIG. 7 shows a schematic diagram of a circular reference object with a circularity greater than a preset threshold according to the present disclosure.

Referring to FIG. 6 and FIG. 7, FIG. 6 shows a schematic diagram of a first to-be-measured human-face image including a circular reference object with a circularity greater than a preset threshold according to the present disclosure, and FIG. 7 shows a schematic diagram of a circular reference object according to the present disclosure. The pixel value g of the standard major axis (the diameter in the longest direction of the circular reference object) of the circular reference object in the photograph is identified, the pixel value k of the circular reference object in the direction $I_1$ in the first to-be-measured human-face image is identified, and the pixel value i of the circular reference object in the direction $I_2$ in the first to-be-measured human-face image is identified. It is easily obtained that the pixel value g of the standard major axis of the circular reference object is equal to the pixel value of the diameter when there is no angle of inclination (the camera and the face plane are parallel). It can be understood that the pixel value k is equal to the projection of the pixel value g of the major axis in the direction $I_1$, and the pixel value i is equal to the projection of the pixel value g of the major axis in the direction $I_2$. Accordingly, the horizontal angle of inclination and the vertical angle of inclination may be determined by using the following formulas:

$$\cos\alpha = \frac{k}{g},\ \cos\beta = \frac{i}{g} \tag{5}$$

$$\alpha = \arccos\frac{k}{g},\ \beta = \arccos\frac{i}{g} \tag{6}$$

Optionally, in the present embodiment, the step of, according to the first pixel value, the second pixel value and the actual size of the preset reference object, determining the first size of the first to-be-measured human face includes but is not limited to: according to the first pixel value, the second pixel value, the horizontal angle of inclination, the vertical angle of inclination and the actual size, determining the first size.

Particularly, when the circular reference object is a 1 yuan coin, the diameter of the 1 yuan coin is 22.25 mm. In FIG. 4, according to the proportion relation between the actual size and the pixel value of the 1 yuan coin, it may be easily obtained that the projection distance in $I_1$ between the centers of the two eyes is $$\frac{22.25}{g}d,$$

and accordingly the true distance in the space between the centers of the two eyes is:

$$D = \frac{22.25}{g}d \div \cos\alpha \tag{7}$$

By substituting the $$\cos\alpha = \frac{k}{g}$$

in the formula (5) into formula (7), it is obtained that:

$$D = \frac{22.25}{g}d \div \frac{k}{g} = \frac{22.25d}{k} \tag{8}$$

Likewise, based on FIG. 5, it can be obtained that:

$$A = \frac{22.25a}{i}, B = \frac{22.25b}{i}, C = \frac{22.25c}{i} \tag{9}$$

Optionally, in the present embodiment, before the step of collecting the first to-be-measured human-face image of the to-be-measured target, the method further includes but is not limited to: on an image previewing interface of the first image collecting device for collecting the first to-be-measured human-face image, exhibiting an auxiliary line, where the auxiliary line is used to indicate the spatial position and the image-collection angle of the first image collecting device.

Particularly, in order to effectively reduce the error generated in the collection of the human-face image of the to-be-measured target at an image-collection angle as a non-standard angle, a photographing assisting means may be provided in the first image collecting device. For example, when the human-face image of the to-be-measured target is being collected, an auxiliary line is exhibited in a preview frame of the lens image, to guide the user to adjust the position of the camera, to reduce the horizontal angle of inclination and the vertical angle of inclination. The auxiliary line may be a horizontal line, to guide the user to, in photographing, make his eyes to flush with the horizontal line, and may also be a rectangular auxiliary line or circular auxiliary line that has the similar function, so as to place the preset reference object within the area of the auxiliary line and so on.

Optionally, in the present embodiment, the circular reference object includes but is not limited to an iris in the first to-be-measured human-face image.

The present embodiment includes collecting a first to-be-measured human-face image of a to-be-measured target, where the first to-be-measured human-face image includes a first to-be-measured human face of the to-be-measured target and a circular reference object; acquiring a first pixel value of the first to-be-measured human face, and a second pixel value of the circular reference object; in response to a circularity of the circular reference object being greater than a preset circularity threshold, acquiring an angle of inclination of the circular reference object; and according to the first pixel value, the second pixel value, the angle of inclination and an actual size of the circular reference object, determining a first size of the first to-be-measured human face. By using the proportion relation between the actual size and the pixel value in the first to-be-measured human-face image of the circular reference object, and according to the angle of inclination of the circular reference object, the first size of the first to-be-measured human face is determined, which simplifies the steps of the measuring operation in the related art, and increases the accuracy of the measurement on the human-face size.

The Second Method Embodiment

Figure 8:
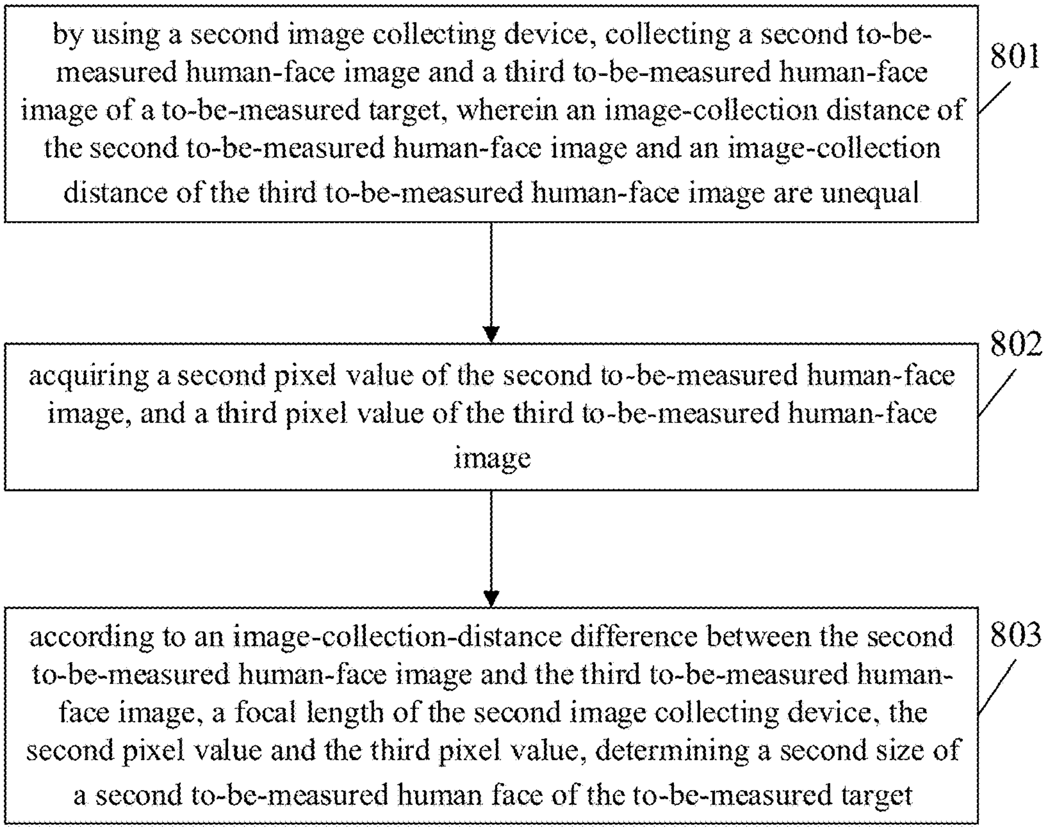
FIG. 8 shows a flow chart of the second embodiment of the method for determining a human-face size according to the present disclosure.

Referring to FIG. 8, FIG. 8 shows a flow chart of the second embodiment of the method for determining a human-face size according to the present disclosure. The method may particularly include:

Step 801: by using a second image collecting device, collecting a second to-be-measured human-face image and a third to-be-measured human-face image of a to-be-measured target, where an image-collection distance of the second to-be-measured human-face image and an image-collection distance of the third to-be-measured human-face image are unequal;

Step 802: acquiring a second pixel value of the second to-be-measured human-face image, and a third pixel value of the third to-be-measured human-face image; and Step 803: according to an image-collection-distance difference between the second to-be-measured human-face image and the third to-be-measured human-face image, a focal length of the second image collecting device, the second pixel value and the third pixel value, determining a second size of a second to-be-measured human face of the to-be-measured target.

In the present embodiment, the collected second to-be-measured human-face image and third to-be-measured human-face image of the to-be-measured target include but are not limited to a photograph of the whole or a local part of a human body. The second to-be-measured human-face image or the third to-be-measured human-face image includes the second to-be-measured human face that is required to be measured, for example, a photograph of the full body, a photograph of the upper half body, a photograph of the head or the face, and so on, of a human body. In the present embodiment, the particular photograph type is not limited in any form.

The second image collecting device according to the present embodiment generally collects a planar image of the to-be-measured target, and the second image collecting device includes but is not limited to a photo camera, a video camera and other devices that have the function of image collection. It should be noted that, in the process of the second image collecting device collecting the second to-be-measured human-face image and the third to-be-measured human-face image of the to-be-measured target, the image-collection distances of the collection of the second to-be-measured human-face image and the collection of the third to-be-measured human-face image are unequal, but the image-collection angles are equal. In order to maintain the accuracy of the acquired second human-face size, it is required to maintain the camera and the human-face plane of the second to-be-measured human face to be parallel.

Furthermore, optionally, the present embodiment includes but is not limited to the second to-be-measured human-face image and the third to-be-measured human-face image that are obtained by performing twice collection at unequal distances by the second image collecting device, and may also include at least two human-face images that are obtained by performing at least twice collection at unequal distances by the second image collecting device, for example, the second to-be-measured human-face image, the third to-be-measured human-face image and another to-be-measured human-face image that are obtained by collection at three unequal distances. By collecting the plurality of to-be-measured human-face images, the accuracy of the second to-be-measured human face that is actually measured is increased, thereby reducing the error.

Figure 9:
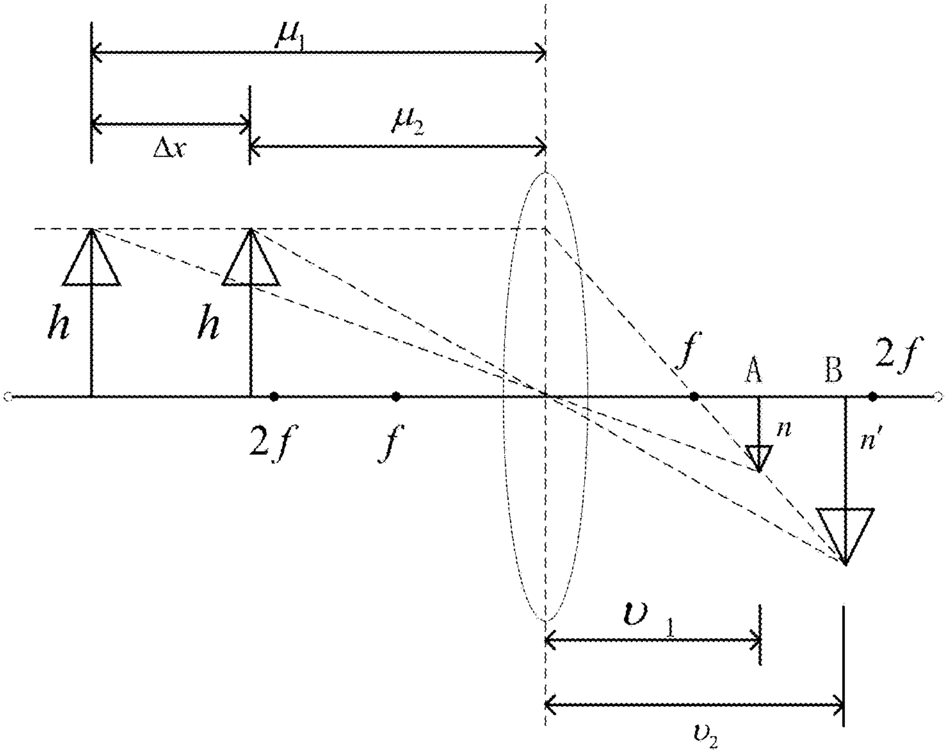
FIG. 9 shows a schematic diagram of the collection of the to-be-measured human-face image by the second image collecting device at different image-collection distances according to the present disclosure.

Referring to FIG. 9, FIG. 9 shows a schematic diagram of the collection of the to-be-measured human-face image by the second image collecting device at different image-collection distances according to the present disclosure. The camera in the image collecting device is essentially a convex lens. The point where parallel light rays converge after passing through the convex lens is referred to as the focal point, and the distance from the focal point to the center of the convex lens is referred to as the focal length, which is expressed by the letter f. The focal length f of a camera is decided by the curvature of the convex lens itself, and convex lenses of different curvatures have different focal lengths f. The focal lengths f of the cameras of commonly used video cameras or photo cameras may be obtained from the specification of the product or from the manufacturer, or may be preset. In the image collection, the distance from the to-be-measured target to the center of the convex lens of the camera is the image-collection distance $\mu$, and the distance from the roll film (the imaging position) to the center of the convex lens of the camera is the image distance v. When the second image collecting device is operating, the object is beyond 2 times the focal length ($\mu>2f$), and the roll film (the imaging position) is between 1 times the focal length and 2 times the focal length ($f<v<2f$), to form an upside-down and reduced image.

In the example in FIG. 9, when a specified object of the size h in the second to-be-measured human face of the to-be-measured target is at the position 1 whose image-collection distance is $\mu_1$, the size of the image at the point A is n, in which case the image distance is $v_1$. When it is at the position 2 whose image-collection distance is $\mu_2$, the size of the image at the point B is n', in which case the image distance is $v_2$. According to the principle of convex-lens imaging, it may be obtained that:

$$\frac{1}{\mu_1}+\frac{1}{v_1}=\frac{1}{f} \tag{10}$$

$$\frac{1}{\mu_2}+\frac{1}{v_2}=\frac{1}{f} \tag{11}$$

In FIG. 9, according to the principle of similitude of right triangles, it may be obtained that:

$$\frac{\mu_1}{v_1}=\frac{h}{n} \tag{12}$$

$$\frac{\mu_2}{v_2}=\frac{h}{n'} \tag{13}$$

In most cases, the measurement on the image-collection distances $\mu_1$ and $\mu_2$ is difficult. If it is defined that the difference between the two image-collection distances is:

$$\Delta X=\mu_1-\mu_2 \tag{14}$$

Then, by simultaneously solving the formulas (10)-(14), the object size may be obtained:

$$h=\frac{\Delta X}{f}\cdot\frac{nn'}{n'-n},\ \mu_2=\frac{v_2\Delta X}{f}\cdot\frac{n}{n'-n} \tag{15}$$

It can be known from the formula (15) that it is merely required to measure the difference $\Delta X$ between the image-collection distances, and the sizes n and n' of the same object in the photographs collected in two different images, and the true size of the specified object in the second to-be-measured human face may be estimated. It can be understood that, when the object size h is the sizes of multiple features in the face surface of the patient, the true sizes of the multiple features may be individually estimated.

In practical application scenes, when there is not a high requirement on the size precision, the image distance $v_2$ is approximately equal to the focal length f($v_2\approx f$). The image-collection distance from the specified object to the camera may be estimated as follows:

$$\mu_2=\frac{n}{n'-n}\Delta X \tag{16}$$

If the specified object is a certain tiny feature of the to-be-measured target, the distance from the tiny feature to the photo camera may be estimated.

Likewise, the image-collection distances from each of the tiny features (for example, point features and line features) of the face of the to-be-measured target to the photo camera may be estimated. By performing data processing to the image-collection distances from each of the point features and the line features of the face of the to-be-measured target to the camera, a 3D contour diagram of the face of the to-be-measured target may be obtained, to obtain the second size of the second to-be-measured human face of the to-be-measured target.

Optionally, in the present embodiment, the step of, by using the second image collecting device, collecting the second to-be-measured human-face image and the third to-be-measured human-face image of the to-be-measured target incudes but is not limited to: according to a first position sensor in the second image collecting device, and a second position sensor in the to-be-measured target, determining the image-collection-distance difference.

Particularly, the first position sensor and the second position sensor are provided in the second image collecting device and the to-be-measured target respectively, a first image-collection distance corresponding to the second to-be-measured human-face image and a second image-collection distance corresponding to the third to-be-measured human-face image are determined by using the first position sensor and the second position sensor, and subsequently the difference between the first image-collection distance and the second image-collection distance is acquired.

It should be noted that the first position sensor and the second position sensor according to the present embodiment include but are not limited to an alignment sensor, an infrared sensor and so on. When the first position sensor and the second position sensor are alignment sensors, by using the first position sensor and the second position sensor, the real-time positions of the image collecting device and the to-be-measured target may be determined respectively, thereby determining the image-collection-distance difference. Moreover, when the first position sensor and the second position sensor are infrared sensors, the distance between the first position sensor and the second position sensor may be acquired, thereby determining the image-collection-distance difference. In the present embodiment, the particular types of the first position sensor and the second position sensor are not limited in any form.

Optionally, in the present embodiment, the step of, by using the second image collecting device, collecting the second to-be-measured human-face image and the third to-be-measured human-face image of the to-be-measured target includes but is not limited to: after collecting the second to-be-measured human-face image by using the second image collecting device, controlling the second image collecting device to move by a first distance, where the first distance is equal to the image-collection-distance difference; or after collecting the second to-be-measured human-face image by using the second image collecting device, controlling the to-be-measured target to move by the first distance.

Particularly, in the present embodiment, the image-collection distance may be changed in two modes. The first mode is to maintain the position of the to-be-measured target unchanged, and move the second image collecting device relative to the to-be-measured target by the first distance. The second mode is to maintain the position of the second image collecting device unchanged, and control the to-be-measured target to be moved relative to the second image collecting device by the first distance. It should be noted that, after the second image collecting device or the to-be-measured target is moved by the first distance, it is required to maintain the camera of the second image collecting device and the human-face plane of the to-be-measured target to be parallel.

The present embodiment includes by using a second image collecting device, collecting a second to-be-measured human-face image and a third to-be-measured human-face image of a to-be-measured target, where an image-collection distance of the second to-be-measured human-face image and an image-collection distance of the third to-be-measured human-face image are unequal; acquiring a second pixel value of the second to-be-measured human-face image, and a third pixel value of the third to-be-measured human-face image; and according to an image-collection-distance difference between the second to-be-measured human-face image and the third to-be-measured human-face image, a focal length of the second image collecting device, the second pixel value and the third pixel value, determining a second size of a second to-be-measured human face of the to-be-measured target. By photographing the plurality of human-face images of the to-be-measured target at unequal image-collection distances, and subsequently using the image-collection-distance difference and the pixel values of the different human-face images, the second size of the second to-be-measured human face is determined, which further increases the accuracy of the measurement on the human-face size.

The Third Method Embodiment

Figure 10:
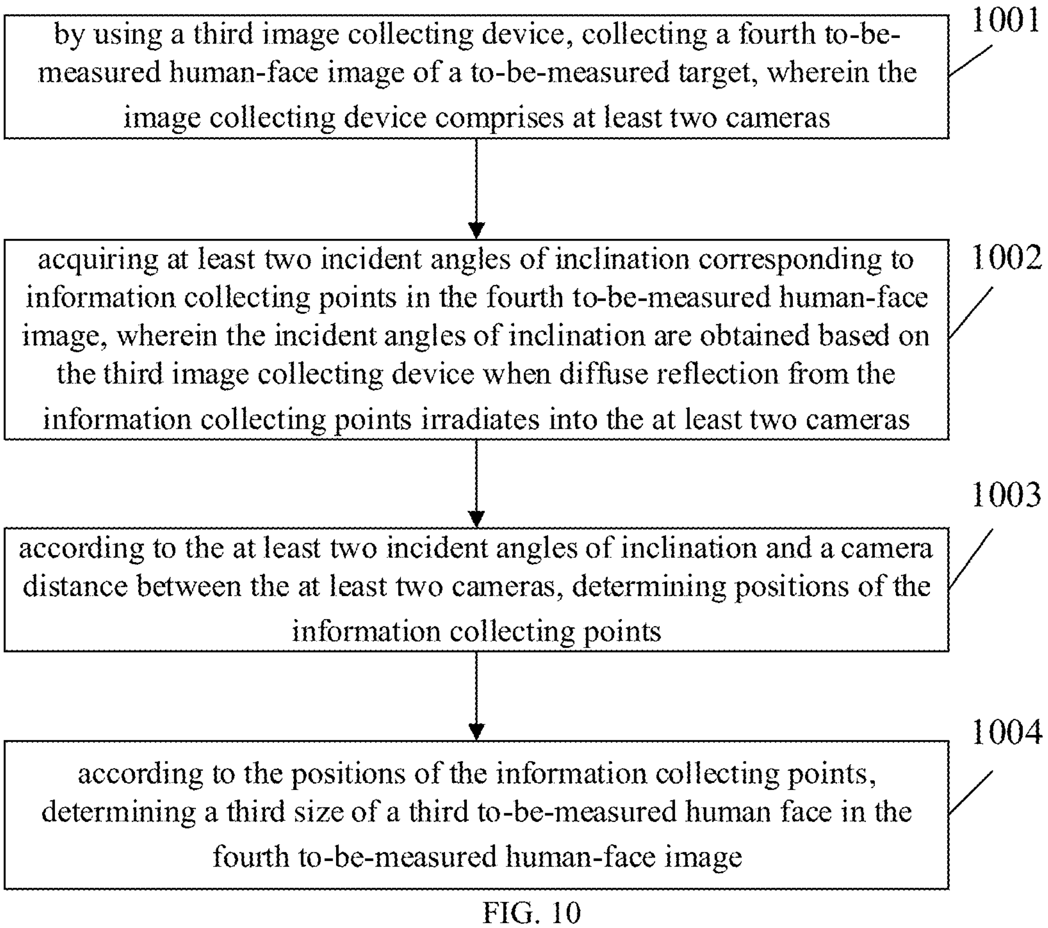
FIG. 10 shows a flow chart of the third embodiment of the method for determining a human-face size according to the present disclosure.

Referring to FIG. 10, FIG. 10 shows a flow chart of the third embodiment of the method for determining a human-face size according to the present disclosure. The method may particularly include:

Step 1001: by using a third image collecting device, collecting a fourth to-be-measured human-face image of a to-be-measured target, where the image collecting device includes at least two cameras;

Step 1002: acquiring at least two incident angles of inclination corresponding to information collecting points in the fourth to-be-measured human-face image, where the incident angles of inclination are obtained based on the third image collecting device when diffuse reflection from the information collecting points irradiates into the at least two cameras;

Step 1003: according to the at least two incident angles of inclination and a camera distance between the at least two cameras, determining positions of the information collecting points; and Step 1004: according to the positions of the information collecting points, determining a third size of a third to-be-measured human face in the fourth to-be-measured human-face image.

In the present embodiment, the fourth to-be-measured human-face image includes but is not limited to a photograph of the whole or a local part of a human body. The fourth to-be-measured human-face image includes the third to-be-measured human face that is required to be measured, for example, a photograph of the full body, a photograph of the upper half body, a photograph of the head or the face, and so on, of a human body. In the present embodiment, the particular photograph type is not limited in any form.

The third image collecting device according to the present embodiment includes but is not limited to a photo camera, a video camera and other devices that have the function of image collection. The third image collecting device includes at least two cameras, and the cameras have the function of data processing, and may acquire the incident angles of inclination of light rays. Preferably, the at least two cameras in the third image collecting device are arranged according to a predetermined layout. For example, when the image collecting device is a double-camera image collecting device, the straight line where the connecting line between the two cameras is located is a straight line in the vertical or horizontal direction, and is parallel to the plane where the human face of the to-be-measured target is located. Moreover, when the image collecting device is an image collecting device having three or more cameras, all of the three or more cameras are provided in the same plane, and are arranged at the positions of the vertexes of a polygon, where the quantity of the sides of the polygon is equal to the quantity of the cameras. For example, in an image collecting device having three cameras, the three cameras are arranged at the positions of the vertexes of a triangle. Four cameras are arranged at the positions of the vertexes of a square.

The cameras in the third image collecting device according to the present embodiment have the function of data processing, and may acquire the incident angles of inclination of light rays. Practically, by using the position layout of the cameras in the third image collecting device, the distance between the plurality of cameras may be acquired, and, subsequently, by using the distance between the plurality of cameras and the information collecting points in the human face of the to-be-measured target, the positions of the information collecting points may be determined.

In particular application scenes, a plurality of information collecting points are provided in advance in the human face of the to-be-measured target, and, by acquiring the positions of the plurality of information collecting points, a three-dimensional 3D model of the human face of the to-be-measured target is established. The quantity and the particular positions of the information collecting points may be set according to practical experience. For example, the information collecting points are configured according to the requirements of breathing masks in practical applications, for example, the two-eye distance, the distance from the nasal tip to the human eyes, the bridge height, and so on, in the human face, which is not limited in any form in the present embodiment.

Optionally, in the present embodiment, the third image collecting device includes a first camera and a second camera, and the information collecting points include a first end point and a second end point of a preset connecting line of the fourth to-be-measured human-face image; and the step of acquiring the at least two incident angles of inclination corresponding to the information collecting points in the fourth to-be-measured human-face image includes but is not limited to: acquiring an incident angle of inclination corresponding to the first end point and an incident angle of inclination corresponding to the second end point, where the preset connecting line is parallel to a connecting line between the first camera and the second camera.

Particularly, when the third image collecting device has merely two cameras, the acquired distances from the information collecting points to the first camera and to the second camera are actually relative distances. The connecting line formed by the first camera and the second camera is parallel to the preset connecting line, and the information collecting points in the preset connecting line are located in the plane formed by the first camera, the second camera, the first end point and the second end point. By acquiring the incident angles of inclination corresponding to the at least two information collecting points in the preset connecting line, i.e., the first end point and the second end point, by using the double-camera third image collecting device, the relative positions of the first end point and the second end point are determined.

Optionally, in the present embodiment, the step of acquiring the incident angle of inclination corresponding to the first end point and the incident angle of inclination corresponding to the second end point includes but is not limited to: acquiring a first incident angle of inclination of irradiation from the first end point into the first camera, and a second incident angle of inclination of irradiation from the first end point into the second camera; and acquiring a third incident angle of inclination of irradiation from the second end point into the first camera, and a fourth incident angle of inclination of irradiation from the second end point into the second camera.

Figure 11:
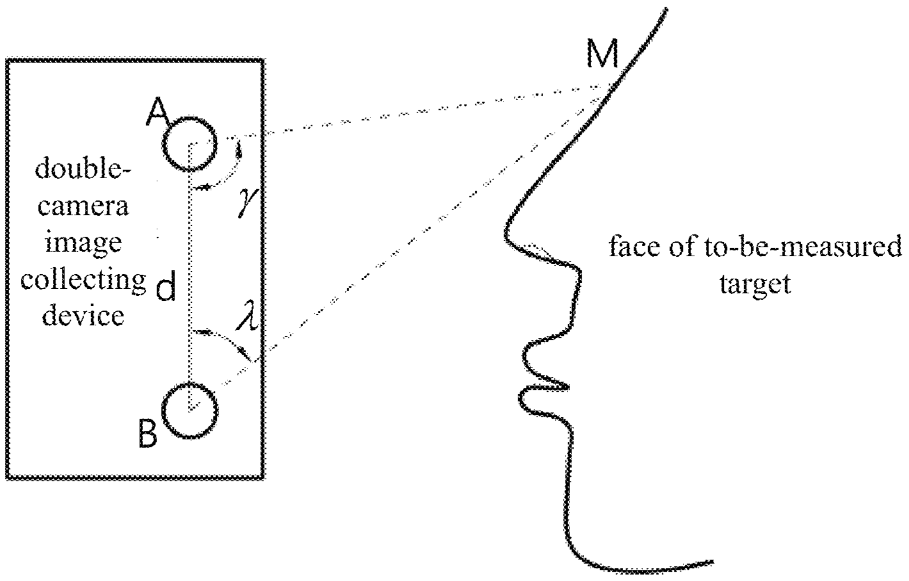
FIG. 11 shows a schematic diagram of a method for acquiring incident angles of inclination of information collecting points based on a double-camera image collecting device according to the present disclosure.

Particularly, referring to FIG. 11, FIG. 11 shows a schematic diagram of a method for acquiring incident angles of inclination of information collecting points based on a double-camera image collecting device according to the present disclosure. By using a double-lens processing system, the size information of the to-be-measured target is obtained. The double-camera image collecting device includes a camera A and a camera B, and has the function of data processing. The distance between the camera A and the camera B is used as a known condition, and is expressed by the letter d. The camera A and the camera B can capture light rays, and sense the incident angles of inclination of the light rays. The first end point M of the preset connecting line in the face of the to-be-measured target is taken, and the light rays that it diffusively reflects individually enter the camera A and the camera B. The camera A captures the light ray MA from the first end point M, and calculates to obtain its incident angle of inclination γ. The camera B captures the light ray MB from the first end point M, and calculates to obtain its incident angle of inclination A. Based on the same logic and calculation mode as those of the first end point M, the incident angle of inclination of the second end point of the preset connecting line may be obtained similarly, which is not discussed further herein.

Optionally, in the present embodiment, the step of, according to the at least two incident angles of inclination and the camera distance between the at least two cameras, determining the positions of the information collecting points includes but is not limited to: according to the first incident angle of inclination, determining a first distance between the first end point and the first camera, and according to the first incident angle of inclination, determining a second distance between the first end point and the second camera; according to the second incident angle of inclination, determining a third distance between the second end point and the first camera, and according to the second incident angle of inclination, determining a fourth distance between the second end point and the second camera; based on a straight line where the first camera and the second camera are located, establishing a plane coordinate system; based on the plane coordinate system, according to the first distance, the second distance, the first incident angle of inclination, the second incident angle of inclination and the camera distance, determining a plane-coordinate position of the first end point; and based on the plane coordinate system, according to the third distance, the fourth distance, the third incident angle of inclination, the fourth incident angle of inclination and the camera distance, determining a plane-coordinate position of the second end point.

Figure 12:
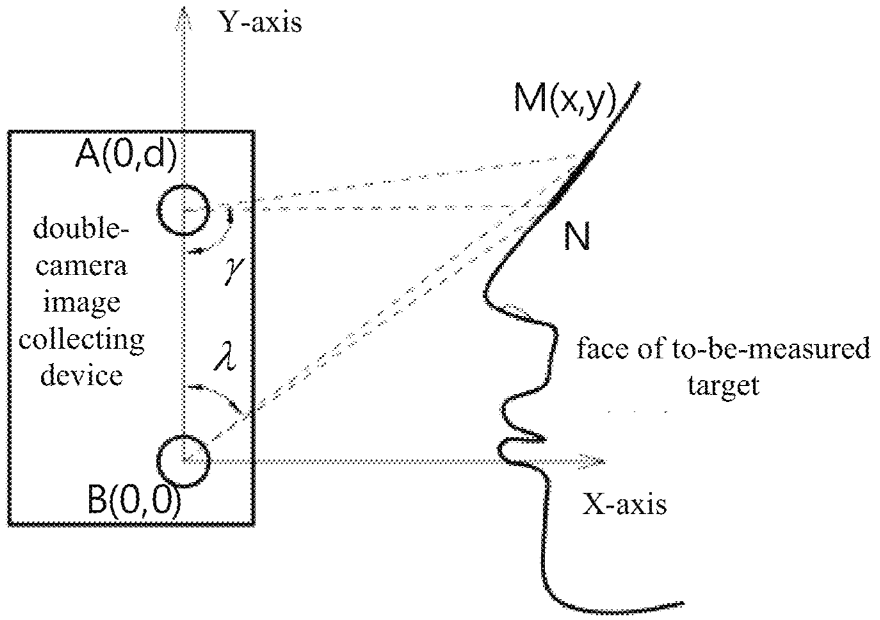
FIG. 12 shows a schematic diagram of the distance between a plurality of information collecting points acquired based on a double-camera image collecting device according to the present disclosure.

Particularly, referring to FIG. 12, FIG. 12 shows a schematic diagram of the distance between the first end point and the second end point acquired based on a double-camera image collecting device according to the present disclosure. The example in FIG. 11 gives the method for acquiring the incident angles of inclination of the first end point M and the second end point N. In FIG. 12, taking the first end point M as an example, a triangle MAB is established in the plane, and, accordingly, by using the triangle sine law, it may be obtained that:

$$|MA| = \frac{d\sin\lambda}{\sin\gamma\cos\lambda + \cos\gamma\sin\lambda} \tag{17}$$

$$|MB| = \frac{d\sin\gamma}{\sin\gamma\cos\lambda + \cos\gamma\sin\lambda} \tag{18}$$

In order to further determine the position of the first end point M, the present disclosure provides the following preferable logical-calculation method. By using the camera B as the origin of coordinates, using the direction of the connecting line between the camera B and the camera A as the Y-axis direction, and using the normal direction of the connecting line between the camera B and the camera A as the X-axis direction, a rectangular plane coordinate system XOY is established (FIG. 10). It can be understood that the coordinate of the point of the camera B is (0,0), and the coordinate of the point of the camera A is (0,d). It is set that the coordinate of the information collecting point M is (x,y), and accordingly the following vector relation may be obtained:

$$BA=(0,d);\ BM=(x,y);\ AB=(0,-d);\ AM=(x,y-d) \tag{19}$$

$$\cos\lambda=\frac{BA\cdot BM}{|BA|\cdot|BM|}=\frac{dy}{d\cdot\sqrt{x^2+y^2}}=\frac{y}{\sqrt{x^2+y^2}} \tag{20}$$

$$\cos\gamma=\frac{AB\cdot AM}{|AB|\cdot|AM|}=\frac{-dy+d^2}{d\cdot\sqrt{x^2+(y-d)^2}}=\frac{-y+d}{\sqrt{x^2+(y-d)^2}} \tag{21}$$

By simultaneously solving the formulas (20)-(21), it may be obtained that:

$$x=\frac{d\tan\gamma\tan\lambda}{\tan\gamma-\tan\lambda} \tag{22}$$

$$y=\frac{d\tan\gamma}{\tan\gamma-\tan\lambda} \tag{23}$$

In other words, the position coordinate of the first end point M in the coordinate system XOY is $$\left(\frac{d\tan\gamma\tan\lambda}{\tan\gamma-\tan\lambda},\ \frac{d\tan\gamma}{\tan\gamma-\tan\lambda}\right).$$

By using the same logical-calculation method, the position coordinate of the second end point N of the face of the patient can be obtained, which is not discussed further in the present embodiment.

Optionally, in the present embodiment, the step of, according to the positions of the information collecting points, determining the third size of the third to-be-measured human face in the fourth to-be-measured human-face image includes but is not limited to: acquiring a pixel value of the preset connecting line and a pixel value of the second to-be-measured human face in the fourth to-be-measured human-face image; according to the plane-coordinate position of the first end point and the plane-coordinate position of the second end point, determining a size of the preset connecting line; and according to the size of the preset connecting line, the pixel value of the preset connecting line and the pixel value of the third to-be-measured human face, determining the third size.

Particularly, in an example, if the coordinate of the second end point N is set to be (m,n), then the position coordinate of the second end point N in the coordinate system XOY may be obtained, and in turn it may be obtained that the distance between the first end point M and the second end point N of the preset connecting line in the face of the to-be-measured target is:

$$|MN|=\sqrt{(x-m)^2+(y-n)^2} \tag{24}$$

In other words, by using the above-described double-lens processing system, the distance between any two information collecting points in the face of the to-be-measured target may be obtained, to determine the third size of the third to-be-measured human face, which is used to instruct the to-be-measured target to select a suitable face mask, or used to manufacture a suitable face mask.

Optionally, in the present embodiment, the third image collecting device includes at least three cameras, and the at least three cameras are located in a same plane; the fourth to-be-measured human-face image includes a plurality of information collecting points, and the information collecting points are allocated into the fourth to-be-measured human-face image according to a preset density threshold; and the step of acquiring the at least two incident angles of inclination corresponding to the information collecting points in the fourth to-be-measured human-face image when the diffuse reflection irradiates into the at least two cameras includes but is not limited to: acquiring at least three incident angles of inclination corresponding to the information collecting points.

Figure 13:
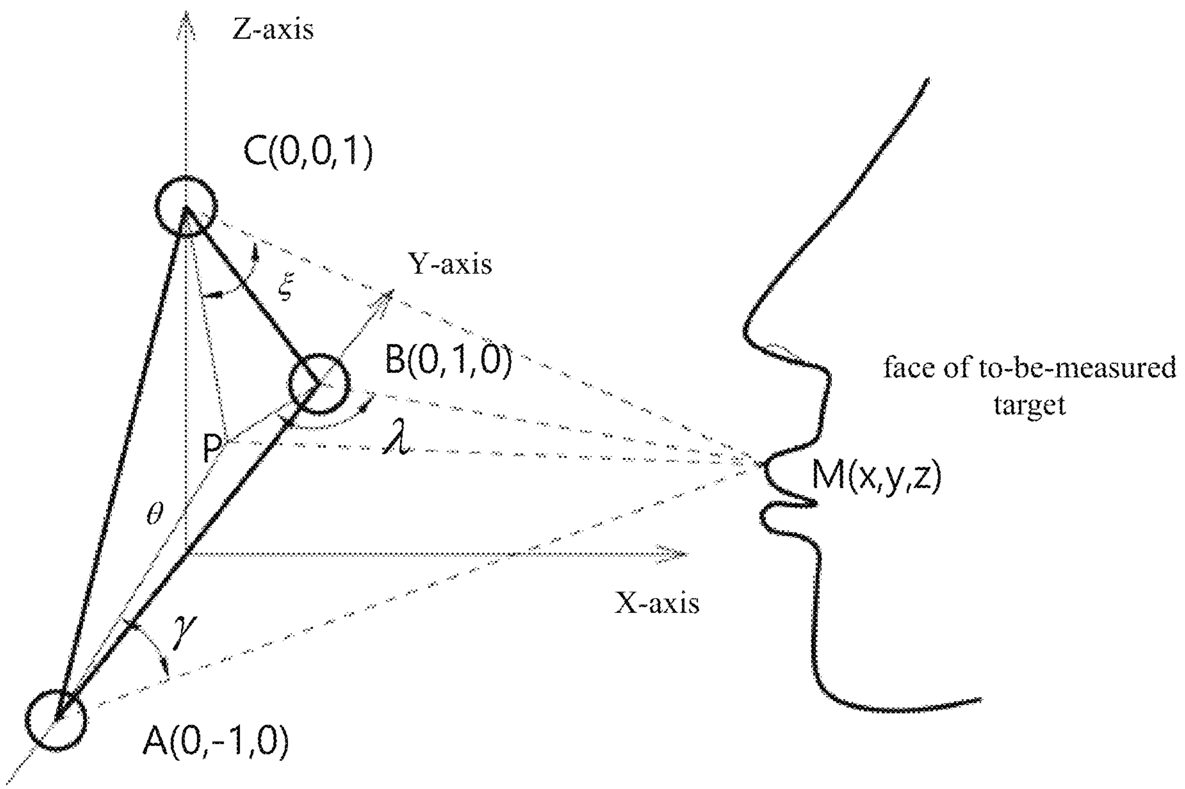
FIG. 13 shows a schematic diagram of a method for determining a human-face size based on a three-camera image collecting device according to the present disclosure.

Particularly, referring to FIG. 13, FIG. 13 shows a schematic diagram of a method for determining a human-face size based on a three-camera image collecting device according to the present disclosure. The third image collecting device includes a camera A, a camera B and a camera C, and has the function of data processing. The plane where the camera A, the camera B and the camera C are located is marked by using the Greek letter θ. The camera A, the camera B and the camera C can capture light rays, and sense the incident angles of inclination of the light rays relative to the plane θ. One information collecting point M is randomly taken in the face of the to-be-measured target, and the light rays that it diffusively reflects individually enter the camera A, the camera B and the camera C. The camera A captures the light ray MA from the information collecting point M, and calculates to obtain its incident angle of inclination γ relative to the plane θ. The camera B captures the light ray MB from the information collecting point M, and calculates to obtain its incident angle of inclination λ relative to the plane θ. The camera C captures the light ray MC from the information collecting point M, and calculates to obtain its incident angle of inclination ζ relative to the plane θ.

Optionally, in the present embodiment, the step of, according to the at least two incident angles of inclination and the camera distance between the at least two cameras, determining the positions of the information collecting points includes but is not limited to: acquiring at least three distances between each of the information collecting points and the at least three cameras; according to a plane where the at least three cameras are located, establishing a space coordinate system; and based on the space coordinate system, according to camera distances between the at least three cameras and the at least three incident angles, determining space coordinate positions of the information collecting points.

Particularly, still taking the example in FIG. 13 as an example for the description, in order to conveniently determine the position of the information collecting point M, the present embodiment provides the following preferable logical-calculation method. A space rectangular coordinate system is established, and it is defined that the coordinate positions of the camera A, the camera B and the camera C are A (0,−1,0), B (0,1,0) and C (0,0,1) respectively. It is set that the coordinate of the information collecting point M is (x,y,z), it may be easily known that the projection point of the information collecting point M in the plane θ is P (0,y,z). Accordingly, the following vector relations can be obtained:

$$AP=(0,y+1,z);\ AM=(x,y+1,z); \tag{25}$$

-continued $$BP=(0,y-1,z);\ BM=(x,y-1,z); \tag{26}$$

$$CP=(0,y,z-1);\ CM=(x,y,z-1) \tag{27}$$

$$\cos\gamma=\frac{AP\cdot AM}{|AP|\cdot|AM|}=\frac{(y+1)^2+z^2}{\sqrt{(y+1)^2+z^2}\cdot\sqrt{x^2+(y+1)^2+z^2}} \tag{28}$$

$$\cos\lambda=\frac{BP\cdot BM}{|BP|\cdot|BM|}=\frac{(y-1)^2+z^2}{\sqrt{(y-1)^2+z^2}\cdot\sqrt{x^2+(y-1)^2+z^2}} \tag{29}$$

$$\cos\xi=\frac{CP\cdot CM}{|CP|\cdot|CM|}=\frac{y^2+(z-1)^2}{\sqrt{y^2+(z-1)^2}\cdot\sqrt{x^2+y^2+(z-1)^2}} \tag{30}$$

By simultaneously solving the formulas (28)-(30), the values of x, y and z can be obtained, or, in other words, the space coordinate position of the information collecting point M is obtained.

Optionally, in the present embodiment, the step of, according to the positions of the information collecting points, determining the third size of the third to-be-measured human face in the fourth to-be-measured human-face image includes but is not limited to: based on the space coordinate positions corresponding to the plurality of information collecting points, establishing a human-face model of the third to-be-measured human face, to determine the third size.

Figure 14:
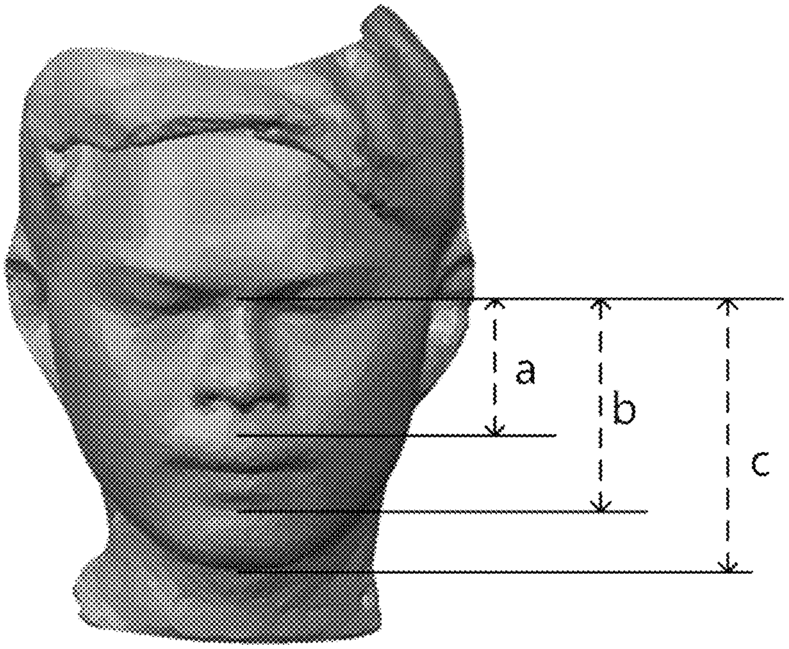
FIG. 14 shows a schematic diagram of a human-face model of a to-be-measured target according to an embodiment of the present disclosure.

Particularly, referring to FIG. 14, FIG. 14 shows a schematic diagram of a human-face model of a to-be-measured target according to an embodiment of the present disclosure. In the present embodiment, the curved surface of the face of the to-be-measured target is formed by combining a plurality of information collecting points, and, particularly, the quantity of the information collecting points may be set according to practical experience. All of the data from the information collecting points in the face of the to-be-measured target are collected and calculated by the third image collecting device of a three-lens processing system, which acquires the space coordinate positions of each of the information collecting points, which can in turn form a human-face 3D model of the face of the to-be-measured target. In particular application scenes, the human-face 3D model may be used by a computer to automatically identify particular size information, which is used to select a face mask matching with the face of the to-be-measured target. Certainly, it may also be used to, according to the 3D model of the face of the to-be-measured target, design a personalized face mask.

It should be noted that, in particular application scenes, especially regarding a to-be-measured target having a malformed face, by designing a matching face mask according to the face information of the to-be-measured target, the sealing property and the wearing comfortableness are effectively improved.

The present embodiment includes by using a third image collecting device, collecting a fourth to-be-measured human-face image of a to-be-measured target, where the image collecting device includes at least two cameras; acquiring at least two incident angles of inclination corresponding to information collecting points in the fourth to-be-measured human-face image; according to the at least two incident angles of inclination and a camera distance between the at least two cameras, determining positions of the information collecting points; and according to the positions of the information collecting points, determining a third size of a third to-be-measured human face in the fourth to-be-measured human-face image. That avoids manually measuring the human face by using a scale ruler, which simplifies the measuring operation. Moreover, by photographing the fourth to-be-measured human-face image by using a plurality of lenses, the third size of the third to-be-measured human face can be determined based on the camera distance between the cameras, which ensures the accuracy of the measurement on the human-face size.

The Fourth Method Embodiment

The present embodiment further provides a method for determining a face-mask size. The method may particularly include the following steps:

Step S1: by using the method for determining a human-face size according to any one or more of the first method embodiment, the second method embodiment and the third method embodiment, obtaining a target human-face size; and Step S2: according to a plurality of groups of preset face-mask reference values and the target human-face size, determining a face-mask model of the to-be-measured target, where the plurality of groups of preset face-mask reference values correspond to a plurality of face-mask models.

The target human-face size is obtained by using the methods in the first method embodiment, the second method embodiment or the third method embodiment, and the particular process of acquiring the target human-face size is not discussed further in the present embodiment.

Subsequently, in particular application scenes, the face masks of different models correspond to different human-face-size ranges, and each of the human-face-size ranges corresponds to one group of preset face-mask reference values. If the relevant parameters of the target human-face size fall within the human-face-size range corresponding to the preset face-mask reference values, then it is determined that the face-mask model corresponding to the current preset face-mask reference values is the face-mask model matching with the to-be-measured target.

Particularly, in the present embodiment, the face-mask reference values include but are not limited to the parameters such as the nose width, the first distance between the two inner canthi in the face, and the second distance between the eyebrow center and the philtrum. The particular types of the parameters of the face sites may be set according to practical experience, and are not limited in any form in the present embodiment.

Optionally, in the present embodiment, each of the groups of the face-mask reference values includes a first reference value corresponding to a first human-face site and a second reference value corresponding to a second human-face site, and the target human-face size includes a plurality of site sizes corresponding to the first face site and the second face site; and the step of, according to the plurality of groups of preset face-mask reference values and the target human-face size, determining the face-mask model of the to-be-measured target includes but is not limited to: in response to the site size corresponding to the first face site matching with the first reference value, determining the face-mask model corresponding to the first reference value.

In particular application scenes, the face sites of the human face are classified according to the gas-tightness priorities, where the face site that has a higher gas-tightness priority and/or a higher comfortableness weight value is classified as the first face site, and the face site that has a lower gas-tightness priority and/or a lower comfortableness weight value is classified as the second face site. If the gas-tightness priority is higher, the face mask has a better gas tightness, and if the comfortableness weight value is higher, the user has a higher comfortableness.

In the present embodiment, because all of the reference values corresponding to the different sites are different, the face sites in the target human face might not completely match with the reference values of one face-mask model. In this case, the corresponding face-mask model is determined according to the first reference value matching with the first face site, to ensure the gas tightness and the comfortableness of the face mask.

Optionally, in the present embodiment, the step of, according to the plurality of groups of preset face-mask reference values and the target human-face size, determining the face-mask model of the to-be-measured target includes but is not limited to: in response to the plurality of site sizes in the target human-face size completely matching with the plurality of reference values in the face-mask reference values, selecting the face-mask model corresponding to the face-mask reference values; or in response to the plurality of site sizes in the target human-face size partially matching with the plurality of reference values in the face-mask reference values, when a quantity of the matched reference values is greater than or equal to a preset quantity threshold, selecting the face-mask model corresponding to the face-mask reference values.

Particularly, in the present embodiment, the step of, according to the plurality of groups of preset face-mask reference values and the target human-face size, determining the face-mask model of the to-be-measured target includes matching a plurality of site sizes in the target human-face size and a plurality of site reference values in the face-mask reference values; in response to the plurality of site sizes in the target human-face size completely matching with the plurality of reference values in the face-mask reference values, selecting the face-mask model corresponding to the face-mask reference values; and in response to the plurality of site sizes in the target human-face size partially matching with the plurality of reference values in the face-mask reference values, when a quantity of the matched reference values is greater than or equal to a preset quantity threshold, selecting the face-mask model corresponding to the face-mask reference values.

In an example, the nose width, the first distance between the two inner canthi in the face, and the second distance between the eyebrow center and the philtrum in the target human-face size are matched with the face-mask reference values. If all of the nose width, the first distance and the second distance match with the site reference values of a face-mask model A, then it is determined that the face-mask model matching with the target person is the model A. If the nose width matches with the site reference value corresponding to the face-mask model A, and both of the first distance and the second distance match with the site reference values of a face-mask model B, then it is determined that the face-mask model matching with the target person is the model B.

In the above embodiment, by, according to a plurality of groups of preset face-mask reference values and the target human-face size, determining a face-mask model of the to-be-measured target, the gas tightness and the comfortableness of the face mask are ensured.

The First Device Embodiment

Figure 15:
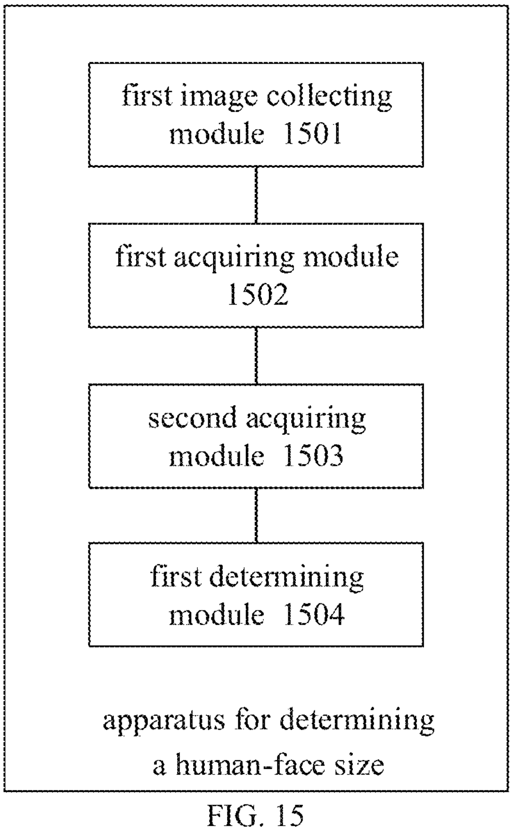
FIG. 15 shows a structural block diagram of the first embodiment of the apparatus for determining a human-face size according to the present disclosure.

Referring to FIG. 15, FIG. 15 shows a structural block diagram of the first embodiment of the apparatus for determining a human-face size according to the present disclosure. The apparatus may particularly include:

1) a first image collecting module 1501 configured for collecting a first to-be-measured human-face image of a to-be-measured target, where the first to-be-measured human-face image includes a first to-be-measured human face of the to-be-measured target and a circular reference object;
2) a first acquiring module 1502 configured for acquiring a first pixel value of the first to-be-measured human face, and a second pixel value of the circular reference object;
3) a second acquiring module 1503 configured for, in response to a circularity of the circular reference object being greater than a preset circularity threshold, acquiring an angle of inclination of the circular reference object; and
4) a first determining module 1504 configured for, according to the first pixel value, the second pixel value, the angle of inclination and an actual size of the circular reference object, determining a first size of the first to-be-measured human face.

Optionally, the particular examples of the present embodiment may refer to the examples described above with respect to the first process embodiment, and are not discussed further in the present embodiment.

The Second Device Embodiment

Figure 16:
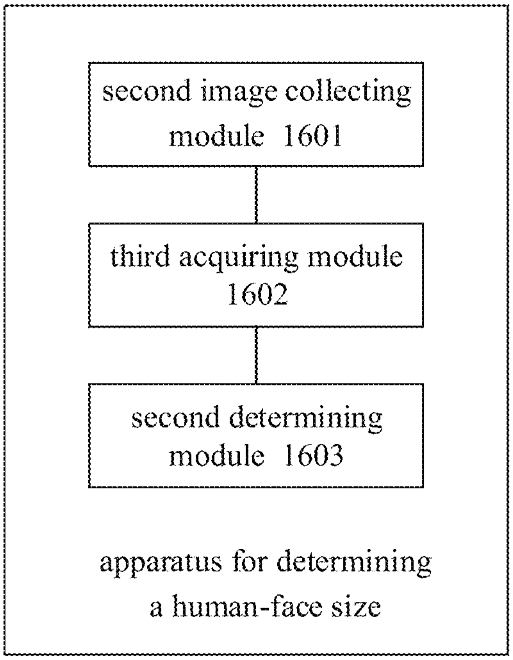
FIG. 16 shows a structural block diagram of the second embodiment of the apparatus for determining a human-face size according to the present disclosure.

Referring to FIG. 16, FIG. 16 shows a structural block diagram of the second embodiment of the apparatus for determining a human-face size according to the present disclosure. The apparatus may particularly include:

1) a second image collecting module 1601 configured for, by using a second image collecting device, collecting a second to-be-measured human-face image and a third to-be-measured human-face image of a to-be-measured target, where an image-collection distance of the second to-be-measured human-face image and an image-collection distance of the third to-be-measured human-face image are unequal;
2) a third acquiring module 1602 configured for acquiring a second pixel value of the second to-be-measured human-face image, and a third pixel value of the third to-be-measured human-face image; and
3) a second determining module 1603 configured for, according to an image-collection-distance difference between the second to-be-measured human-face image and the third to-be-measured human-face image, a focal length of the second image collecting device, the second pixel value and the third pixel value, determining a second size of a second to-be-measured human face of the to-be-measured target.

Optionally, the particular examples of the present embodiment may refer to the examples described above with respect to the second process embodiment, and are not discussed further in the present embodiment.

The Third Device Embodiment

Figure 17:
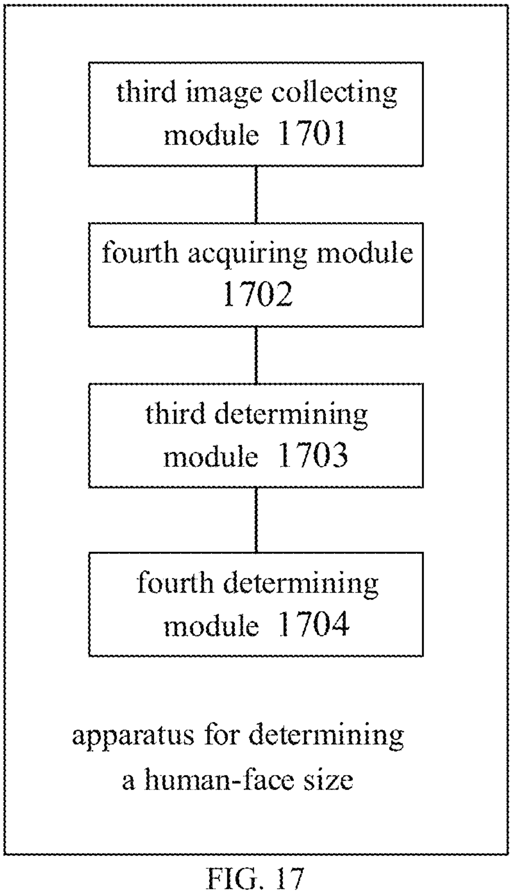
FIG. 17 shows a structural block diagram of the third embodiment of the apparatus for determining a human-face size according to the present disclosure.

Referring to FIG. 17, FIG. 17 shows a structural block diagram of the third embodiment of the apparatus for determining a human-face size according to the present disclosure. The apparatus may particularly include:

1) a third image collecting module 1701 configured for, by using a third image collecting device, collecting a fourth to-be-measured human-face image of a to-be-measured target, where the third image collecting device includes at least two cameras;

2) a fourth acquiring module 1702 configured for acquiring at least two incident angles of inclination corresponding to information collecting points in the fourth to-be-measured human-face image, where the incident angles of inclination are obtained based on the third image collecting device when diffuse reflection from the information collecting points irradiates into the at least two cameras;

3) a third determining module 1703 configured for, according to the at least two incident angles of inclination and a camera distance between the at least two cameras, determining positions of the information collecting points; and 4) a fourth determining module 1704 configured for, according to the positions of the information collecting points, determining a third size of a third to-be-measured human face in the fourth to-be-measured human-face image.

Optionally, the particular examples of the present embodiment may refer to the examples described above with respect to the third process embodiment, and are not discussed further in the present embodiment.

The Fourth Device Embodiment

The present embodiment further provides an apparatus for determining a face-mask model, where the apparatus includes:

1) an acquiring unit configured for, by using the apparatus for determining a human-face size according to any one of the first device embodiment, the second device embodiment and the third device embodiment, obtaining a target human-face size; and 2) a determining unit configured for, according to a plurality of groups of preset face-mask reference values and the target human-face size, determining a face-mask model of the to-be-measured target, where the plurality of groups of preset face-mask reference values correspond to a plurality of face-mask models.

Optionally, the particular examples of the present embodiment may refer to the examples described above with respect to the fourth process embodiment, and are not discussed further in the present embodiment.

Regarding the device embodiments, because they are substantially similar to the process embodiments, they are described simply, and the related parts may refer to the description on the process embodiments.

The embodiments of the description are described in the mode of progression, each of the embodiments emphatically describes the differences from the other embodiments, and the same or similar parts of the embodiments may refer to each other.

The particular modes of the operations performed by the modules of the apparatus according to the above embodiments have already been described in detail in the embodiments of the method, and will not be explained and described in detail herein.

Figure 18:
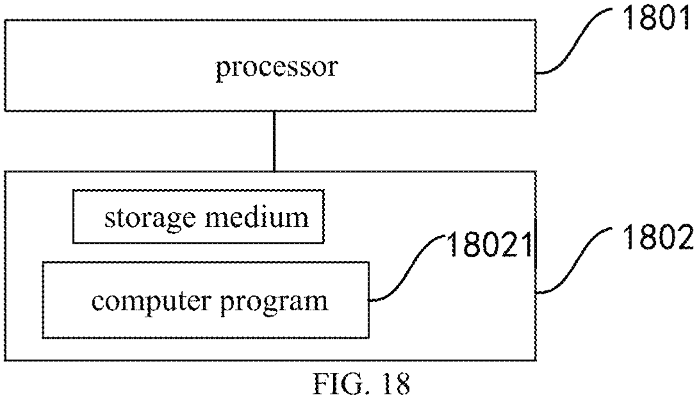
FIG. 18 shows a structural block diagram of an electronic device according to the present disclosure.

An embodiment of the present application further provides an electronic device. Referring to FIG. 18, the electronic device includes a processor 1801, a memory 1802 and a computer program 18021 that is stored in the memory and is executable in the processor, where the processor, when executing the computer program, implements the method for determining a human-face size according to the above embodiments.

An embodiment of the present application further provides a readable storage medium, where when an instruction in the storage medium is executed by a processor of an electronic device, the electronic device is able to implement the method for determining a human-face size according to the above embodiments.

Regarding the device embodiments, because they are substantially similar to the process embodiments, they are described simply, and the related parts may refer to the description on the process embodiments.

The algorithms and displaying provided herein are not inherently related to any particular computer, virtual system or other devices. Various general-purpose systems may be used with the teachings disclosed herein. On the basis of the above description, the structure required to construct such a type of systems is apparent. Furthermore, the embodiments of the present application are not limited to any specific programming language. It should be understood that the contents of the embodiments of the present application described herein may be implemented by using various programming languages, and the description above for a specific language is intended to disclose the most preferable embodiments of the embodiments of the present application.

The description provided herein describes many concrete details. However, it can be understood that the embodiments of the present application may be implemented without those concrete details. In some of the embodiments, well-known processes, structures and techniques are not described in detail, so as not to affect the understanding of the description.

Similarly, it should be understood that, in order to simplify the present application and facilitate to comprehend one or more of the aspects of the present application, in the above description on the exemplary embodiments of the embodiments of the present application, the features of the embodiments of the present application are sometimes grouped into individual embodiments, figures or the descriptions thereon. However, the method that is disclosed should not be interpreted as reflecting the intention that the embodiments of the present application that are claimed require more feature than the features that are explicitly set forth in each of the claims. More precisely, as reflected by the following claims, the aspects of the present application are less than all of the features of the individual embodiments that are disclosed above. Therefore, the claims which follow a particular embodiment are accordingly explicitly incorporated into the particular embodiment, and each of the claims itself serves as a separate embodiment of the embodiments of the present application.

A person skilled in the art can understand that the modules in the device according to an embodiment may be self-adaptively modified and be provided in one or more devices that are different from that embodiment. The modules or units or components in the embodiments may be combined into one module or unit or component, and may also be divided into multiple submodules or subunits or subcomponents. Unless at least some of such features and/or processes or units are mutually rejected, all of the features that are disclosed by the description (including the accompanying claims, the abstract and the drawings) and all of the processes or units of any method or device that is disclosed herein may be combined in any combination. Unless explicitly stated otherwise, each of the features that are disclosed by the description (including the accompanying claims, the abstract and the drawings) may be replaced by alternative features that provide the same, equivalent or similar objects.

Each component embodiment of the embodiments of the present application may be implemented by hardware, or by software modules that are operated in one or more processors, or by a combination thereof. A person skilled in the art should understand that some or all of the functions of some or all of the components of the device according to the embodiments of the present application may be implemented by using a microprocessor or a digital signal processor (DSP) in practice. The embodiments of the present application may also be implemented as apparatus or device programs for implementing part of or the whole of the method described herein. Such programs for implementing the embodiments of the present application may be stored in a computer-readable medium, or may be in the form of one or more signals. Such signals may be downloaded from an Internet website, or provided on a carrier signal, or provided in any other forms. It should be noted that the above embodiments are for describing the embodiments of the present application, rather than limiting the embodiments of the present application, and a person skilled in the art may design alternative embodiments without departing from the scope of the appended claims.

In the claims, any reference signs between parentheses should not be construed as limiting the claims. The word "include" does not exclude elements or steps that are not listed in the claims. The word "a" or "an" preceding an element does not exclude the existing of a plurality of such elements. The embodiments of the present application may be implemented by means of hardware including several different elements and by means of a properly programmed computer. In unit claims that list several devices, some of those devices may be embodied by the same item of hardware. The words first, second, third and so on do not denote any order. Those words may be interpreted as names.

A person skilled in the art can clearly understand that, in order for the convenience and concision of the description, the particular working processes of the above-described systems, devices and units may refer to the corresponding processes according to the above-described process embodiments, and are not discussed herein further.

The above description is merely preferable embodiments of the embodiments of the present application, and is not indented to limit the embodiments of the present application. Any modifications, equivalent substitutions and improvements that are made within the spirit and the principle of the embodiments of the present application should fall within the protection scope of the embodiments of the present application.

The above are merely particular embodiments of the embodiments of the present application, and the protection scope of the embodiments of the present application is not limited thereto. All of the variations or substitutions that a person skilled in the art can easily envisage within the technical scope disclosed by the embodiments of the present application should fall within the protection scope of the embodiments of the present application. Therefore, the protection scope of the embodiments of the present application should be subject to the protection scope of the claims.

What is claimed is:

1. A method for determining a human-face size, wherein the method comprises:

collecting a first to-be-measured human-face image of a to-be-measured target, wherein the first to-be-measured human-face image comprises a first to-be-measured human face of the to-be-measured target and a circular reference object;

acquiring a first pixel value of the first to-be-measured human face, and a second pixel value of the circular reference object;

in response to a circularity of the circular reference object being greater than a preset circularity threshold, acquiring an angle of inclination of the circular reference object; and according to the first pixel value, the second pixel value, the angle of inclination and an actual size of the circular reference object, determining a first size of the first to-be-measured human face;

wherein the step of, in response to the circularity of the circular reference object being greater than the preset circularity threshold, acquiring the angle of inclination of the circular reference object comprises:

acquiring a standard major axis of the circular reference object, wherein the standard major axis refers to, in response to the circularity being greater than the preset circularity threshold, a longest diameter in the circular reference object;

acquiring a first major axis in a first direction and a second major axis in a second direction in the circular reference object, wherein the first direction refers to a straight line where a connecting line between centers of two eyes in the first to-be-measured human-face image is located, and the second direction refers to a straight line where a connecting line between an eyebrow center and a nasal tip in the first to-be-measured human-face image is located;

according to the standard major axis and the first major axis, determining a horizontal angle of inclination of the circular reference object; and according to the standard major axis and the second major axis, determining a vertical angle of inclination of the circular reference object.

2. The method according to claim 1, wherein the method further comprises:

in response to the circularity being less than or equal to the preset circularity threshold, according to the first pixel value, the second pixel value and the actual size, determining the first size.

3. The method according to claim 1, wherein the step of, according to the first pixel value, the second pixel value, the angle of inclination and the actual size of the circular reference object, determining the first size of the first to-be-measured human face comprises:

according to the first pixel value, the second pixel value, the horizontal angle of inclination, the vertical angle of inclination and the actual size, determining the first size.

4. The method according to claim 1, wherein the circular reference object comprises an iris in the first to-be-measured human-face image.

5. A method for determining a face-mask model, wherein the method comprises:

by using the method for determining the human-face size according to claim 1, obtaining a target human-face size; and according to a plurality of groups of preset face-mask reference values and the target human-face size, determining a face-mask model of the to-be-measured target, wherein the plurality of groups of preset face-mask reference values correspond to a plurality of face-mask models.

6. The method according to claim 5, wherein each of the plurality of groups of preset face-mask reference values comprises a first reference value corresponding to a first human-face site of a face mask and a second reference value corresponding to a second human-face site of the face mask, and the target human-face size comprises a plurality of site sizes corresponding to a first face site of a target human-face and a second face site of the target human-face; and the step of, according to the plurality of groups of preset face-mask reference values and the target human-face size, determining the face-mask model of the to-be-measured target comprises:

in response to the site size corresponding to the first face site of the target human-face matching with the first reference value, determining the face-mask model corresponding to the first reference value.

7. The method according to claim 6, wherein the step of, according to the plurality of groups of preset face-mask reference values and the target human-face size, determining the face-mask model of the to-be-measured target comprises:

in response to the plurality of site sizes in the target human-face size completely matching with a plurality of site reference values in one group of preset face-mask reference values, selecting the face-mask model corresponding to the one group of preset face-mask reference values; or in response to the plurality of site sizes in the target human-face size partially matching with the plurality of site reference values in the one group of preset face-mask reference values, when a quantity of the matched site reference values is greater than or equal to a preset quantity threshold, selecting the face-mask model corresponding to the one group of preset face-mask reference values.

8. A non-transitory computer-readable storage medium, wherein the non-transitory computer-readable storage medium stores a computer program, wherein the computer program comprises a computer-readable code, and when the computer-readable code is executed in an electronic device, the computer-readable code causes the electronic device to implement the method for determining the human-face size according to claim 1.

9. The computer program according to claim 8, wherein the operations further comprise:

in response to the circularity being less than or equal to the preset circularity threshold, according to the first pixel value, the second pixel value and the actual size, determining the first size.

10. The computer program according to claim 8, wherein the operation of, according to the first pixel value, the second pixel value, the angle of inclination and the actual size of the circular reference object, determining the first size of the first to-be-measured human face comprises:

according to the first pixel value, the second pixel value, the horizontal angle of inclination, the vertical angle of inclination and the actual size, determining the first size.

11. The computer program according to claim 8, wherein the circular reference object comprises an iris in the first to-be-measured human-face image.

12. An electronic device, wherein the electronic device comprises:

a memory storing a computer-readable code; and at least one processor, wherein when the computer-readable code is executed by the at least one processor, a computing and processing device implements operations comprising:

collecting a first to-be-measured human-face image of a to-be-measured target, wherein the first to-be-measured human-face image comprises a first to-be-measured human face of the to-be-measured target and a circular reference object;

acquiring a first pixel value of the first to-be-measured human face, and a second pixel value of the circular reference object;

in response to a circularity of the circular reference object being greater than a preset circularity threshold, acquiring an angle of inclination of the circular reference object; and according to the first pixel value, the second pixel value, the angle of inclination and an actual size of the circular reference object, determining a first size of the first to-be-measured human face;

wherein the operation of, in response to the circularity of the circular reference object being greater than the preset circularity threshold, acquiring the angle of inclination of the circular reference object comprises:

acquiring a standard major axis of the circular reference object, wherein the standard major axis refers to, in response to the circularity being greater than the preset circularity threshold, a longest diameter in the circular reference object;

acquiring a first major axis in a first direction and a second major axis in a second direction in the circular reference object, wherein the first direction refers to a straight line where a connecting line between centers of two eyes in the first to-be-measured human-face image is located, and the second direction refers to a straight line where a connecting line between an eyebrow center and a nasal tip in the first to-be-measured human-face image is located;

according to the standard major axis and the first major axis, determining a horizontal angle of inclination of the circular reference object; and according to the standard major axis and the second major axis, determining a vertical angle of inclination of the circular reference object.

13. The electronic device according to claim 12, wherein the operations further comprise:

in response to the circularity being less than or equal to the preset circularity threshold, according to the first pixel value, the second pixel value and the actual size, determining the first size.

14. The electronic device according to claim 12, wherein the operation of, according to the first pixel value, the second pixel value, the angle of inclination and the actual size of the circular reference object, determining the first size of the first to-be-measured human face comprises:

according to the first pixel value, the second pixel value, the horizontal angle of inclination, the vertical angle of inclination and the actual size, determining the first size.

15. The electronic device according to claim 12, wherein the circular reference object comprises an iris in the first to-be-measured human-face image.

* * * * *